US007910108B2

(12) United States Patent
Friedman et al.

(10) Patent No.: US 7,910,108 B2
(45) Date of Patent: Mar. 22, 2011

(54) SHEDDASE INHIBITORS COMBINED WITH CD30-BINDING IMMUNOTHERAPEUTICS FOR THE TREATMENT OF CD30 POSITIVE DISEASES

(75) Inventors: Steven M. Friedman, West Chester, PA (US); Robert C. Newton, Avondale, PA (US); Peggy A. Scherle, Media, PA (US); Krishna Vaddi, Kennett Square, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 11/757,600

(22) Filed: Jun. 4, 2007

(65) Prior Publication Data

US 2007/0280943 A1    Dec. 6, 2007

Related U.S. Application Data

(60) Provisional application No. 60/811,308, filed on Jun. 5, 2006.

(51) Int. Cl.
*A61K 39/395* (2006.01)
(52) U.S. Cl. .................................. 424/155.1; 424/178.1
(58) Field of Classification Search .................. None
See application file for complete search history.

(56) References Cited

U.S. PATENT DOCUMENTS

| | | | |
|---|---|---|---|
| 4,474,893 A | 10/1984 | Reading | |
| 4,486,414 A | 12/1984 | Pettit | |
| 4,714,681 A | 12/1987 | Reading | |
| 4,785,119 A | 11/1988 | Hojo et al. | |
| 4,816,444 A | 3/1989 | Pettit et al. | |
| 4,879,278 A | 11/1989 | Pettit et al. | |
| 4,879,315 A | 11/1989 | Magarian et al. | |
| 4,925,648 A | 5/1990 | Hansen et al. | |
| 4,973,593 A | 11/1990 | Brubaker | |
| 4,978,744 A | 12/1990 | Pettit et al. | |
| 4,986,988 A | 1/1991 | Pettit et al. | |
| 5,076,973 A | 12/1991 | Pettit et al. | |
| 5,138,036 A | 8/1992 | Pettit et al. | |
| 5,157,034 A | 10/1992 | Bright et al. | |
| 5,182,288 A | 1/1993 | Murray et al. | |
| 5,410,024 A | 4/1995 | Pettit et al. | |
| 5,494,919 A | 2/1996 | Morriello et al. | |
| 5,504,191 A | 4/1996 | Pettit et al. | |
| 5,521,284 A | 5/1996 | Pettit et al. | |
| 5,530,097 A | 6/1996 | Pettit et al. | |
| 5,536,727 A | 7/1996 | Witzel et al. | |
| 5,554,725 A | 9/1996 | Pettit | |
| 5,573,920 A | 11/1996 | Randle | |
| 5,599,902 A | 2/1997 | Pettit et al. | |
| 5,601,819 A | 2/1997 | Wong et al. | |
| 5,610,162 A | 3/1997 | Witzel et al. | |
| 5,635,483 A | 6/1997 | Pettit et al. | |
| 5,663,149 A | 9/1997 | Pettit et al. | |
| 5,665,860 A | 9/1997 | Pettit et al. | |
| 5,763,471 A | 6/1998 | Fourtillan et al. | |
| 5,770,573 A | 6/1998 | Arrhenius et al. | |
| 5,780,454 A | 7/1998 | Adams et al. | |
| 5,780,588 A | 7/1998 | Pettit et al. | |
| 5,872,152 A | 2/1999 | Brown et al. | |
| 5,892,112 A | 4/1999 | Levy et al. | |
| 5,939,598 A | 8/1999 | Kucherlapati et al. | |
| 5,945,430 A | 8/1999 | Doll et al. | |
| 5,968,795 A | 10/1999 | Dixon et al. | |
| 5,972,925 A | 10/1999 | Hohlweg et al. | |
| 6,034,065 A | 3/2000 | Pettit et al. | |
| 6,066,730 A | 5/2000 | Adams et al. | |
| 6,071,901 A | 6/2000 | Dorwald et al. | |
| 6,083,903 A | 7/2000 | Adams et al. | |
| 6,110,913 A | 8/2000 | Dorwald et al. | |
| 6,114,300 A | 9/2000 | Bourdin et al. | |
| 6,235,764 B1 | 5/2001 | Larson et al. | |
| 6,239,104 B1 | 5/2001 | Pettit et al. | |
| 6,239,148 B1 | 5/2001 | Dorwald et al. | |
| 6,249,768 B1 | 6/2001 | Tulskie, Jr. et al. | |
| 6,268,379 B1 | 7/2001 | Xue et al. | |
| 6,297,217 B1 | 10/2001 | Adams et al. | |
| 6,308,162 B1 | 10/2001 | Ouimet et al. | |
| 6,313,117 B1 | 11/2001 | Bekkali et al. | |
| 6,323,315 B1 | 11/2001 | Pettit et al. | |
| 6,372,754 B1 | 4/2002 | Kulagowski | |
| 6,387,371 B1 | 5/2002 | Hudziak et al. | |
| 6,414,130 B1 | 7/2002 | Doherty et al. | |
| 6,429,213 B1 | 8/2002 | Xue et al. | |
| 6,455,472 B1 | 9/2002 | Fischer et al. | |
| 6,465,433 B1 | 10/2002 | Adams et al. | |
| 6,482,838 B2 | 11/2002 | Pratt | |
| 6,489,352 B2 | 12/2002 | Bryans et al. | |
| 6,500,847 B2 | 12/2002 | Van Zandt et al. | |

(Continued)

FOREIGN PATENT DOCUMENTS

CA            2114178        7/1994

(Continued)

OTHER PUBLICATIONS

Matthey et al. (Int. J. Cancer 2004; 111: 568-574).*
Hansen et al. (Journal of Immunology 2000; 165: 6703-6709).*
Friedman, et al., "Clinical Benefit of INCB7839, a potent and selective inhibitor of ADAM10 and ADAM17 in combination with trastuzumab in metastatic HER2 positive breast cancer patients" (San Antonio Breast Cancer Symposium, Dec. 9-13, 2009), 13 pages.*
Millar, et al., "Results of single and repeat dose studies of the oral matrix metalloproteinase inhibitor Inarimastat in healthy male volunteers", Br. J. Pharmacol. 45:21-26 (1998).*

(Continued)

*Primary Examiner* — Sheela J Huff
(74) *Attorney, Agent, or Firm* — Fish & Richardson P.C.

(57) ABSTRACT

The present invention is directed to pharmaceutical methods for the treatment of CD30 positive diseases, such as Hodgkin's disease, by administration of a combination of at least one sheddase inhibitor and at least one anti-CD30 immunotherapeutic.

12 Claims, No Drawings

U.S. PATENT DOCUMENTS

| | | |
|---|---|---|
| 6,528,538 B1 | 3/2003 | Zeiller et al. |
| 6,548,668 B2 | 4/2003 | Adams et al. |
| 6,593,344 B1 | 7/2003 | Biedermann et al. |
| 6,608,104 B2 | 8/2003 | Noe |
| 6,617,317 B1 | 9/2003 | Adams et al. |
| 6,653,312 B1 | 11/2003 | Auvin et al. |
| 6,713,487 B2 | 3/2004 | Yu et al. |
| 6,727,247 B2 | 4/2004 | Flohr et al. |
| 6,747,150 B2 | 6/2004 | Adams et al. |
| 6,858,626 B2 | 2/2005 | Xue et al. |
| 7,013,312 B2 | 3/2006 | Bala et al. |
| 7,307,086 B2 | 12/2007 | Xue et al. |
| 7,340,409 B1 | 3/2008 | Ulwick |
| 7,491,724 B2 | 2/2009 | Li et al. |
| 7,723,349 B2 | 5/2010 | Yao et al. |
| 2002/0042731 A1 | 4/2002 | King et al. |
| 2002/0094989 A1 | 7/2002 | Hale et al. |
| 2002/0161616 A1 | 10/2002 | Chan et al. |
| 2002/0182702 A1 | 12/2002 | Ruben et al. |
| 2003/0069869 A1 | 4/2003 | Gronau et al. |
| 2003/0083263 A1 | 5/2003 | Doronina et al. |
| 2003/0093310 A1 | 5/2003 | Macrae |
| 2003/0158166 A1 | 8/2003 | Thurlimann |
| 2003/0187717 A1 | 10/2003 | Crites et al. |
| 2003/0204440 A1 | 10/2003 | Koller et al. |
| 2003/0212583 A1 | 11/2003 | Perras, Jr. et al. |
| 2004/0006073 A1 | 1/2004 | Dooley |
| 2004/0006215 A1* | 1/2004 | Keler et al. ............ 530/388.22 |
| 2004/0018194 A1 | 1/2004 | Francisco et al. |
| 2004/0034019 A1 | 2/2004 | Tomlinson et al. |
| 2004/0181441 A1 | 9/2004 | Fung et al. |
| 2004/0247602 A1 | 12/2004 | Friedman et al. |
| 2004/0259896 A1* | 12/2004 | Yao et al. ............ 514/278 |
| 2005/0113344 A1 | 5/2005 | Li et al. |
| 2005/0123536 A1 | 6/2005 | Law et al. |
| 2005/0144022 A1 | 6/2005 | Evans |
| 2005/0192302 A1 | 9/2005 | Xue et al. |
| 2005/0250789 A1 | 11/2005 | Burns et al. |
| 2005/0261310 A1 | 11/2005 | Xue et al. |
| 2006/0004018 A1 | 1/2006 | Xue et al. |
| 2006/0020133 A1 | 1/2006 | Xue et al. |
| 2006/0111404 A1 | 5/2006 | Xue et al. |
| 2006/0178920 A1 | 8/2006 | Muell |
| 2007/0055564 A1 | 3/2007 | Fourman |
| 2007/0117809 A1 | 5/2007 | Fridman |
| 2007/0149532 A1 | 6/2007 | Xue |
| 2007/0280943 A1 | 12/2007 | Friedman et al. |
| 2008/0167288 A1* | 7/2008 | Li et al. ............ 514/210.18 |
| 2008/0208528 A1 | 8/2008 | MacGregor |
| 2009/0037241 A1 | 2/2009 | Olsen et al. |
| 2009/0124649 A1* | 5/2009 | Yao et al. ............ 514/278 |

FOREIGN PATENT DOCUMENTS

| | | |
|---|---|---|
| EP | 550025 | 7/1993 |
| EP | 456183 | 10/1995 |
| EP | 937459 | 8/1999 |
| EP | 1369489 | 12/2003 |
| EP | 1415986 | 5/2004 |
| JP | 07300460 | 11/1995 |
| JP | 10-298180 | 11/1998 |
| RU | 200100810 | 11/2001 |
| WO | WO 91/00360 | 1/1991 |
| WO | WO 92/05793 | 4/1992 |
| WO | WO 92/08802 | 5/1992 |
| WO | WO/ 9317715 | 9/1993 |
| WO | WO 93/23040 | 11/1993 |
| WO | WO 93/23041 | 11/1993 |
| WO | WO 94/17038 | 8/1994 |
| WO | WO 96/11924 | 4/1996 |
| WO | WO 96/31470 | 10/1996 |
| WO | WO 96/31473 | 10/1996 |
| WO | WO 96/31474 | 10/1996 |
| WO | WO 96/31498 | 10/1996 |
| WO | WO 96/31500 | 10/1996 |
| WO | WO 96/31503 | 10/1996 |
| WO | WO 96/33176 | 10/1996 |
| WO | WO 98/02151 | 1/1998 |
| WO | WO 98/08850 | 3/1998 |
| WO | WO 98/51665 | 11/1998 |
| WO | WO 98/57932 | 12/1998 |
| WO | WO 99/65867 | 12/1999 |
| WO | WO 00/05265 | 2/2000 |
| WO | WO 00/08046 | 2/2000 |
| WO | WO 00/17158 | 3/2000 |
| WO | WO 00/32193 | 6/2000 |
| WO | WO 00/35451 | 6/2000 |
| WO | WO 00/35453 | 6/2000 |
| WO | WO 00/35876 | 6/2000 |
| WO | WO 00/43383 | 7/2000 |
| WO | WO 00/55143 | 9/2000 |
| WO | WO 00/59502 | 10/2000 |
| WO | WO 00/75137 | 12/2000 |
| WO | WO 01/08669 | 2/2001 |
| WO | WO 01/00616 | 4/2001 |
| WO | WO 01/46166 | 6/2001 |
| WO | WO 01/58891 | 8/2001 |
| WO | WO 01/70673 | 9/2001 |
| WO | WO 01/85669 | 11/2001 |
| WO | WO 01/98306 | 12/2001 |
| WO | WO 02/34716 | 5/2002 |
| WO | WO 02/40481 | 5/2002 |
| WO | WO 02/055491 | 7/2002 |
| WO | WO 02/055516 | 7/2002 |
| WO | WO 02/072106 | 9/2002 |
| WO | WO 02/074754 | 9/2002 |
| WO | WO 02/076945 | 10/2002 |
| WO | WO 02/088172 | 11/2002 |
| WO | WO 02/096426 | 12/2002 |
| WO | WO 03/024456 | 3/2003 |
| WO | WO 03/031431 | 4/2003 |
| WO | WO 03/032914 | 4/2003 |
| WO | WO 03/043661 | 5/2003 |
| WO | WO 03/051840 | 6/2003 |
| WO | WO 03/063845 | 8/2003 |
| WO | WO 03/076430 | 9/2003 |
| WO | WO 03/091220 | 11/2003 |
| WO | WO 03/092606 | 11/2003 |
| WO | WO 2004/020584 | 3/2004 |
| WO | WO 2004/024462 | 3/2004 |
| WO | WO 2004/018453 | 4/2004 |
| WO | WO 2004/034963 | 4/2004 |
| WO | WO 2004/037240 | 5/2004 |
| WO | WO 2004/043349 | 5/2004 |
| WO | WO 2004/050024 | 6/2004 |
| WO | WO 2004/056353 | 7/2004 |
| WO | WO 2004/065361 | 8/2004 |
| WO | WO 2004/089294 | 10/2004 |
| WO | WO 2004/096139 | 11/2004 |
| WO | WO 2004/104086 | 12/2004 |
| WO | WO 2005/001038 | 1/2005 |
| WO | WO 2005/037826 | 4/2005 |
| WO | WO 2005/117882 | 12/2005 |
| WO | WO 2006/039644 | 4/2006 |
| WO | WO 2006039644 | 4/2006 |
| WO | WO 2006/073592 | 7/2006 |
| WO | WO 2007/143600 | 12/2007 |

OTHER PUBLICATIONS

Nemunaitis, et al., "Combined analysis of studies of the effects of the matrix metalloproteinase inhibitor marimastat on serum tumor markers in advanced cancer: selection of a biologically active and tolerable dose for longer-term studies", Clinical Cancer Research, 4:1101-1109 (May 1998).*

Newton, et al., "Clinical Benefit of INCB7839, a potent and selective ADAM inhibitor, in combination with trastuzumab in metastatic HER2+ breast cancer patients" (American Society of Clinical Oncology (Jun. 4-8, 2010), 8 pages.*

Poster entitled "A multicenter phase Ib study of the safety, pharmacokinefics, biological activity and clinical efficacy of INCB7839, a potent and selective inhibitor of ADAM10 and ADAM 17." (Poster #6064, San Antonio Breast Cancer Symposium, Dec. 2007), (enlarged), 12 pages.*

International Search Report for PCT application No. PCT/US2007/070304, mailed Nov. 26, 2007.

Allen, Theresa., "Ligand-Targeted Therapeutics in Anticancer Therapy." *Nature Reviews*, 2:750-765, Oct. 2002.

Amour et al., "The in Vitro Activity of ADAM-10 is Inhibited by TIMP-1 and TIMP-3," *FEBS Letters*, 473(3):275-279, 2000.

Andreesen et al., "Human Microphages Can Express the Hodgkin's Cell-Associated Antigen Ki-1 (CD30)." *The American Journal of Pathology*, 134(1):187-192, Jan. 1989.

Andreesen et al., "A Hodgkin cell-specific antigen is expressed on a subset of auto- and alloactivated T (helper) lymphoblasts." *Blood*, 63:1299-1302, 1984.

Arnon et al., "Monoclonal Antibodies for Immunotargeting of Drugs in Cancer Therapy." *Monoclonal Antibodies and Cancer Therapy*, pp. 243-256, 1985.

Arribas et al., "Protein Ectodomain Shedding", *Chem. Rev.*, 102(12):4627-4638, 2002.

Babine at al., "Molecular Recognition of Protein minus sign Ligand Complexes: Applications to Drug Design", *Chem. Rev.*, 97,(5):1359-1472, 1997.

Baldwin, R. W., and. Byers, Vera, "Monoclonal Antibodies for Cancer Detection and Therapy." pp. 303-316, 1985.

Barth et al., "Ki-4(scFv)-ETA8, a new recombinant anti-CD30 immunotoxin with highly specific cytotoxic activity against disseminated Hodgkin tumors in SCID mice." *Blood*, 95(12):3909-3914, Jun. 15, 2000.

Baselga et al., "Mechanism of Action of anti-HER2 Monoclonal Antibodies", *Annals of Oncology*, 12/Suppl 1):S35-S41, 2001.

Baselga et al., "Mechanism of Action of Trastuzumab and Scientific Updated", *Seminars in Oncology*, 28(5/Suppl 16):4-11, 2001.

Bird et al., "Single-Chain Antigen-Binding Proteins." *Science*, 242(4877):423-426, Oct. 21, 1988.

Buchwald H. et al., "Long-term, Continuous Intravenous Heparin Administration by an Implantable Infusion Pump in Ambulatory Patients with Recurrent Venous Thrombosis", *Surgery*, 88, 4, pp. 507-516, 1980.

Burns, Bruce, and Dardick, Irving, "Ki-1 Positive Non-Hodgkin's Lymphomas." *American Journal of Clinical Pathology*, 93(3):327-332, Mar. 1990.

Carney et al., "Potential Clinical Utility of Serum HER-2/neu Oncoprotein Concentrations in Patients with Breast Cancer", *Clinical Chemistry*, 49(10):1579-1598, 2003.

Chandler et al., "Matrix Metalloproteinases Degrade Myelin Basic Protein", *Neuroscience Lett.*, 201(3):223-226, 1995.

Chari et al., "Irnmunoconjugates Containing Novel Maytansinoids: Promising Anticancer Drugs." *Cancer Research*, 52:127-131, Jan. 1, 1992.

Codony-Servat et al., "Cleavage of the HER2 Ectodomain is a Pervanadate-activable Process that is Inhibited by the tissue Inhibitor of Metalloproteases-1 in Brest Cancer Cells", *Cancer Research*, 59(6):1196-1201, 1999.

Controlled Drug Bioavailability, Drug Product Design and Performance, 1984, Smolen and Ball (eds.), Wiley, New York.

Coussens et al., "Matrix Metalloproteinase Inhibitors and Cancer: Trials and Tribulations", *Science*, 1295:2387-2392, 2002.

During, M.J. et al., "Controlled release of Dopamine from a Polymeric Brain implant: In Vivo Characterization", *Annals Neurology*, . 25, 4, pp. 351, 1989.

Eckert et al., "Follicular Lymphoid Hyperplasia of the Skin with High Content of Ki-1 Positive Lymphocytes." *The American Journal of Dermatopathology*, 11(4):345-352, 1989.

Endo et al., "In Vitro Cytotoxicity of a Human Serum Albumin-mediated Conjugate of Methotrexate with Anti-MM46 Monoclonal Antibody." *Cancer Research*, 47:1076-1080, Feb. 15, 1987.

Engert et al., "Evaluation of Ricin A Chain-containing Immunotoxins Directed against the CD30 Antigen as Potential Reagents for the Treatment of Hodgkin's Disease." *Cancer Research*, 50:84-88, Jan. 1, 1990.

Falini et al., "In vivo targeting of Hodgkin and Reed-Stemberg cells of Hodgkin's disease with monoclonal antibody Ber-H2 (CD30): immunohistological evidence." *British Journal of Haematology*, 82:38-45, 1992.

Falini et al., "Response of refractory Hodgkin's disease to monoclonal anti-CD30 immunotoxin." *The Lancet*, 339:1195-1196, 1992.

Fridman, J.S. et al., "Selective Inhibition of ADAM Metalloproteases as a Novel Approach for Modulating ErbB pathways in Cancer", *Clin Cancer res*, 13, (6) pp. 1892-1901, 2007.

Gallego et al., "Preparation of Four Daunomycin-Monoclonal Antibody 791T/36 Conjugates with Anti-tumor Activity." *Intl. J. Cancer*, 33:737-744, 1984.

Gerli et al., "CD301 T Cells in Rheumatoid Synovitis: Mechanisms of Recruitment and Functional Role." *The Journal of Immunology*, 164:4399-4407, 2000.

Hansen et al., "CD30 Shedding from Karpas 299 Lymphoma Cells IsMediated by TNF-a-Converting Enzyme." *The Journal of Immunology*, 165:6703-6709, 2000.

Hansen et al., "Inhibition of Metalloproteins Enhances the Internalization of Anti-CD30 Antibody Ki-3 and the Cytotoxic Activity of Ki-3 Immunotoxin." *Int. J. Cancer*, 98:210-215, 2002.

Hellman, Samuel., "Principles of Radiation Therapy." *Cancer: Principles and Practice of Oncology $2^{nd}$ Edition*, Chapter 12:227-255, 1985.

Hellstrom et al., "Antibodies for Drug Delivery." *Controlled Drug Delivery*, Chapter 15:624-642, 1987.

Howard III, M.A. et al., "Intracerebral Drug Delivery in Rats with Lesion-induced Memory Deficit" *J. Neurosurg.*, vol. 71, pp. 105, 1989.

Huston et al., "Protein Engineering of Antibody Binding Sites: Recovery of Specific Activity in an Anti-Digoxin Single-Chain Fv Analogue Produced in *Escherichia coli.*" *Proceedings of the National Academy of Sciences of the United States of America*, 85(16):5879-5883, Aug. 15, 1998.

Ihn et al., "Circulating Levels of Soluble CD30 Are Increased in Patients with Localized Scleroderma and Correlated Serological and Clinical Features of the Disease." *The Journal of Rheumatology*, 27(3):698-702, 2000.

*Journal of Pharmaceutical Science*, 66, 2 (1977).

Kaudewitz et al., "Atypical Cells in Lymphomatoid Papulosis Express the Hodgkin's Cell-Associated Antigen Ki-1." *The Journal of Investigative Dermatology*, 86(4):350-354, Apr. 1986.

Kostelney et al., "Formation of a Bispecific Antibody by the use of Leucine Zippers." *The Journal of Immunology*, 148(5):1547-1553, Mar. 1, 1992.

Kuipers et al., "N4-unsubstituted N1-arylpiperazines as High-affinity 5-HT1A Receptor Ligands", *J. Med. Chem.*, 38(11):1942-1954, 1995.

Langer, R. New Methods of Drug Delivery, *Science*, 249: 1527-1533, 1990.

Langer R. and Peppas, N., "Chemical and Physical Structure of Polimers as Carriers for Controlled Release of Bioactive Agents: A Review", *J. Macromol. Sci. Rev. Macromol. Chem.. Phys.*, C23, pp. 61-126, 1983.

Levy, R.J. et al., "Inhibition of Calcification of Bioprosthetic Heart Valves by Local Controlled-Release Diphosphonate", *Science*, vol. 228, pp. 190-192, 1985.

Liu, P.C.C. et al., "Identification of ADAM10 as a Major Source of HER2 Ectodomain Sheddase Activity in HER2 Overexpressing Breast Cancer Cells", *Cancer Biology & Therapy*, 5:6 pp. 657-664, 2006.

Liu, X. et al., "Selective Inhibition of ADAM Metalloproteases blocks HER-2 Extracellular Domain (ECD) Cleavage and Potentiates the Anti-Tumor Effects of Trastuzumab", *Cancer Biology & Therapy*, 5:6 pp. 648-655, 2006.

Matthey et al., "Mettaloproteinase Inhibition Augments Antitumor Efficacy of Anti-CD30 Immunotoxin Ki-3(scFv)-ETA' Against Human Lymphomas in vivo." *Int. J. Cancer*, 111:568-574, 2004.

McMillan et al., "Evaluation of the clinical utility of cerebrospinal fluid (CSF) indices of inflammatory markers in multiple sclerosis." *Acta Neurol Scand.*, 101:239-243, 2000.

Mechterscheimer, Gunhild, and Moeller, Peter, "Expression of Ki-1 Antigen (cD30) in Mesenchymal Tumors." *Cancer*, 66:1732-1737, 1990.

Medical Applications of Controlled Release, 1974, Langer and Wise (eds.), CRC Pres., Boca Raton, Fla.

Miettinen, Markku, "Immunohistochemical Study on Formaldehyde-Fixed, Paraffin-Embedded Hodgkin's and non-Hodgkin's Lymphomas." *Archives of Pathology and Laboratory Medicine*, 116(11):1197-1201, Nov. 1992.

Molina et al., "NH(2) Terminal Tnmcated HER-2 Protein but not Full-Length Receptor is associated with Nodal Metastasis in Human Breast Cancer", *Clinical Cancer Research*, 8(2):347-353, 2002.

Molina et al., "Trastuzumab (herceptin) a Humanized anti-Her2 Receptor Monoclonal Antibody, Inhibits Basal and Activated Her2 Ectodomain Cleavage in Breast Cancer Cells", *Cancer Research*, 61(12):4744-4749, 2001.

Muller, A.J. and Scherle, P.A., "Targeting the Mechanisms of Tumoral Immune Tolerance with Small-molecule Inhibitors" *Nature Reviews Cancer*, 6, pp. 613-626, 2006.

Nadali et al., "Serum Level of the Soluble Form of the CD30 Molecule Identifies Patients With Hodgkin's Disease at High Risk of Unfavorable Outcome." *Blood*, 91(8):3011-3016, Apr. 15, 1998.

Ohkawa et al., "Selective in vitro and in vivo inhibition against human yolk sac tumor cell lines by purified antibody against human α-fetoprotein conjugated with mitomycin C via human serum albumin." *Cancer Immunology Immunotherapy*, 23:81-86, 1986.

Pallesen, G., and Hamilton-Dutoit, S.J., "Ki-1 (CD30) Antigen is Regularly Expressed by Tumor Cells of Embryonal Carcinoma." *American Journal of Pathology*, 133(3):446-450, Dec. 1998.

Pastan, Ira, and Kreitman, Robert, "Overview: Immunotoxins in Cancer Therapy." *Investigational Drugs*, 3(7):1089-1091, 2002.

Payne, Gillian. "Progress in immunoconjugate cancer therapeutics." *Cancer Cell*, 3:207-212, Mar. 2003.

Piris et al., "CD30 Expression in non-Hodgkin's lymphoma." *Histopathology*, 17(3): 211-218, 1990.

*Remington's Pharmaceutical Sciences*, 17th ed., Mack Publishing Company, Easton, Pa., 1985, p. 1418.

Roche, Edward B., Bioreversible Carriers in Drug Design, ed., American Pharmaceutical Association and Pergamon Press, 1987.

Rosendahl et al., "Identification and Characterization of a Pro-tumor Necrosis Factor-alpha-Processing Enzyme from the ADAM Family of Zinc Metalloproteases", *Biol. Chem.*, 272(39):24588-24593, 1997.

Rowland et al. "Drug localization and growth inhibition studies of vindesine-monoclonal anti-CEA conjugates in a human tumor xenograph." *Cancer Immunology Immunotherapy*, 21:183-187, 1986.

Saito et al., "Drug delivery strategy utilizing conjugation via reversible disulfide linkages: role and site of cellular reducing activities." *Advanced Drug Delivery Reviews*, 55:199-215, 2003.

Saudek, C.D. et al., "A Preliminary Trial of the Programmable Medication System for Insulin Delivery", *The New. England. Journal of. Medicine*, 321, pp. 574-579, 1989.

Saus et al., "The Complete Primary Structure of Human Matrix Metalloproteinase-3. Identity with Stromelysin", *J. Biol. Chem.*, 263(14):6742-6745, 1988.

Schnell et al., "Clinical evaluation of ricin A-chain immunotoxins in patients with Hodgkin's lymphoma." *Annals of Oncology*, 14:729-736, 2003.

Schwarting et al., "BER-H2: a new anti-Ki-1 (CD30) monoclonal antibody directed at a formol-resistant epitope." *Blood*, 74:1678-1689, 1989.

Sefton, M.V., "Implantable Pumps" *CRC Crit Rev. Biomed. Eng.* vol. 14, pp. 201-240, 1987.

Senter, Peter, and Springer, Caroline, "Selective activation of anticancer prodrugs by monoclonal antibody—enzyme conjugates." *Advanced Drug .Delivery Reviews*, 53:247-264, 2001.

Stein et al., "The expression of the Hodgkin's disease associated antigen Ki-lin reactive and neoplastic lymphoid tissue: evidence that Reed-Sternberg cells and histiocytic malignancies are derived from activated lymphoid cells." *Blood*, 66:848-858, 1985.

Templeton et al., "Cloning and Characterization of Human Tumor Cell Interstitial Collagenase", *Cancer Research*, 50(17),:5431-5437, 1990.

Thorpe et al, "The Preparation and Cytotoxic Properties of Antibody-Toxin Conjugates", *Immunol. Rev.*, 62:119-58 (1982).

Trail et al., "Monoclonal antibody drug immunoconjugates for targeted treatment of cancer." *Cancer Immunology Immunotherapy*, 52:328-337, 2003.

Treat, J. et al., "Liposome Encapsulated Doxorubicin Preliminary Results of Phase I and Phase II Trials", *Liposomes in the Therapy of Infectious Disease and Cancer*, pp. 353-365, 1989.

Tsutsumi et al., "Site-Specific Chemical Modification with Polyethylene Glycol of Recombinant Immunotoxin Anti-Tac(Fv)-PE38 (LMB-2) Improves Antitumor Activity and Reduces Animal Toxicity and Immunogenicity." *Proceedings of the National Academy of Sciences of the United States of America*, 97(15):8548-8553, Jul. 18, 2000.

Tutt et al., "Trispecific F(ab')₂ Derivatives that Cooperative Signaling via the TCR/CD3 Complex and CD2 to Activate and Redirect Resting Cytotoxic T Cells" *Journal of Immunology*, 147(1):60-69, Jul. 1, 1991.

Ward et al., "Binding Activities of a Repertoire of single immunoglobin variable domains secreted from *Escherichia coli*." *Nature*, 341:544-546, Oct. 12, 1989.

Xue et al., "Rational Design, Synthesis and Structure-activity Relationships of a Cyclic Succinate Series of TNF-alpha Converting Enzyme Inhibitors. Part 1: Lead Identification", *Biorg. Med. Chem. Lett.*, 13(24):4293-4297, 2003.

Xue et al., "Rational Design, Synthesis and Structure-activity Relationships of a Cyclic Succinate Series of TNF-alpha Converting Enzyme Inhibitors. Part 2: Lead Optimization", *Biorg. Med. Chem. Lett.*, 13(24):4299-4304, 2003.

Yao, W. et al., "Discovery of Potent, Slective, and Orally Active Human Epidermal Growth Factor Receptor-2 Sheddase Inhibitor for the Treatment of Cancer", *J. Med. Chem.* 50:603-606, 2007.

Yoshiizumi et al., "Synthesis and Structure-activity Relationship of 5,67,8-tetrahydropyrido[3,4-b]pyrazine-based Hydroxamic Acids as HB-EGF Shedding Inhibitors", *Biorg Med. Chem. Lett.*, 11(3):433:450, 2003.

Zhou, Bin-Bing S. et al., "Targeting ADAM-mediated Ligand Cleavage to Inhibit HER3 and EGFR Pathways in Non-small Cell Lung Cancer", *Cancer Cell*, 10:39-50, 2006.

Zhou, J. et al., "Asymmetric Synthesis of Confonnationally Constrained *trans*-2,3-Piperidine-Dicarboxylic Acid Derivatives", *SYNLETT*, No. 3, pp. 460-464, 2007.

Zhou, B.B., et al., *Expert Opin. Incestig. Drugs*, 14(6):591-606, 2005.

International Search Report for PCT/US2007/070304, dated Oct. 24, 2007.

Amendment in Reply to Office Action dated Jan. 7, 2008 for U.S. Appl. No. 10/817,718.

Amendment and Reply to Office Action dated Nov. 19, 2007 for U.S. Appl. No. 10/965,215 (65 pgs.).

Amendment dated Jan. 14, 2008 for U.S. Appl. No. 10/965,215 (13 pgs.).

Amendment in Reply to Office Action of Jun. 25, 2009 dated Jul. 17, 2009 for U.S. Appl. No. 10/831,265 (17 pgs.).

Amendment for Submission with RCE dated Jun. 20, 2008 for U.S. Appl. No. 10/831,265 (35 pgs.).

Amendment Filed in Connection with RCE dated Dec. 18, 2007 for U.S. Appl. No. 10/831,265 (31 pgs.).

Examination Report dated Jul. 16, 2009 for European Appln. No. 03790120.4 (5 pgs.).

Expert's Opinion received Feb. 8, 2008 for Costa Rican Appln. No. 8045 (28 pgs.).

Final Office Action mailed Aug. 19, 2008 for U.S. Appl. No. 11/014,322 (13 pgs.).

Final Office Action mailed May 30, 2008 for U.S. Appl. No. 11/613,330 (5 pgs.).

Final Office Action mailed Nov. 2, 2007 for U.S. Appl. No. 11/167,329 (4 pgs.).

Final Office Action mailed Nov. 21, 2007 for U.S. Appl. No. 11/167,816 (4 pgs.).

Final Office Action dated Sep. 25, 2007 for U.S. Appl. No. 10/965,215 (6 pgs.).

Non-Final Office Action mailed Apr. 1, 2008 for U.S. Appl. No. 11/167,329 (3 pgs.).

Non-Final Office Action mailed Aug. 22, 2007 for U.S. Appl. No. 11/613,330 (14 pgs.).
Non-Final Office Action mailed Jan. 17, 2008 for U.S. Appl. No. 11/104,041 (4 pgs.).
Non-Final Office Action mailed Jul. 24, 2008 for U.S. Appl. No. 11/104,041 (2 pgs.).
Non-Final Office Action mailed May 16, 2007 for U.S. Appl. No. 11/167,816 (7 pgs.).
Non-Final Office Action mailed May 17, 2007 for U.S. Appl. No. 11/167,329 (7 pgs.).
Non-Final Office Action mailed Oct. 31, 2007 for U.S. Appl. No. 11/014,322 (22 pgs.).
Non-Final Office Action mailed May 17, 2007 for U.S. Appl. No. 10/831,265 (10 pgs.).
Non-Final Office Action mailed Aug. 19, 2009 for U.S. Appl. No. 11/535,795 (6 pgs.).
Non-Final Office Action mailed Oct. 17, 2008 for U.S. Appl. No. 11/602,659 (12 pgs.).
Non-final Office Action dated Mar. 20, 2007 for U.S. Appl. No. 10/965,215 (4 pgs.).
Non-Final Office Action dated Jun. 25, 2009 for U.S. Appl. No. 10/831,265 (5 pgs.).
Notice of Allowance mailed Jun. 25, 2008 for U.S. Appl. No. 11/167,816 (2 pgs.).
Notice of Allowance and Notice of Allowability dated Sep. 23, 2008 for U.S. Appl. No. 10/831,265 (5 pgs.).
Notice of Allowance and Notice of Allowability dated Jan. 17, 2008 for U.S. Appl. No. 10/965,215 (6 pgs.).
Notice of Allowance and Notice of Allowability dated Mar. 25, 2008 for U.S. Appl. No. 10/831,265 (7 pgs.).
Office Action dated Apr. 8, 2008 for U.S. Appl. No. 10/817,718 (20 pgs.).
Office Action dated Oct. 9, 2007 for U.S. Appl. No. 10/817,718 (10 pgs.).
Office Action dated Oct. 19, 2007 for U.S. Appl. No. 10/831,265 (4 pgs.).
Official Action dated Feb. 20, 2008 for Russian Appln. No. 2005136429/04(040664) (three pages; translated).
Office Action mailed Feb. 27, 2009 for Colombian Appln. No. 05-106.414 (5 pgs.).
Office Action mailed Feb. 27, 2009 for Colombian Appln. No. 05-053.243 (6 pgs.).
Opposition dated Jun. 14, 2006 for Costa Rican Appln. No. 8045 (6 pgs.).
Opposition dated Jul. 7, 2006 for Ecuadorian Appln. No. SP-05-5856-PCT (6 pgs.).
Opposition received Jun. 23, 2008 for Costa Rican Appln. No. 8745 (2 pgs.).
Opposition received Jun. 23, 2008 for Costa Rican Appln. No. 8775 (6 pgs.).
Reply in Connection with a Request for Continued Examination dated Apr. 15, 2008 for U.S. Appl. No. 10/965,215 (3 pgs.).
Reply to Action of Oct. 17, 2008 for U.S. Appl. No. 11/602,659 dated Apr. 16, 2009 (9 pgs.).
Response to Office Action dated May 6, 2008 for U.S. Appl. No. 11/104,041 (11 pgs.).
Response to Final Office Action dated Feb.2, 2008 for U.S. Appl. No. 11/167,329 (9 pgs.).
Response to Final Office Action dated Mar. 21, 2008 for U.S. Appl. No. 11/167,816 (8 pgs.).
Response to Non-Final Office Action dated Aug. 16, 2007 for U.S. Appl. No. 11/167,816 (10 pgs.).
Response to Office Action dated Aug. 16, 2007 for U.S. Appl. No. 11/167,329 (9 pgs.).
Response to Office Action dated Dec. 6, 2007 for U.S. Appl. No. 11/014,322 (5 pgs.).
Response to Office Action dated Jan. 22, 2008 for U.S. Appl. No. 11/613,330 (3 pgs.).
Response to Office Action dated Jul. 19, 2007 for U.S. Appl. No. 10/965,215 (79 pgs.).
Search Report dated Jun. 2, 2009 for corresponding Georgian Application No. AP2003008262 (4 pgs.).
Search Report dated Dec. 23, 2008 for Taiwanese Appln. No. 094141007 (1 pg.).
Search Report dated Jan. 30, 2008 for Eurasian Appln. No. 200701782 (2 pgs.).
Search Report for Appln. No. 12005500996 filed in the Philippines (1 pg.).
Search Report dated Nov. 20, 2006 for Georgian Appln. No. AP2004009076 (2 pgs.).
Search Report dated Oct. 6, 2008 for Georgian Appln. No. AP2003008262 (4 pgs).
Supplementary Partial European Search Report dated Jul. 15, 2008 for European Appln. No. 04760368 (2 pgs.).
International Preliminary Report on Patentability mailed May 22, 2007 for International Application No. PCT/US2005/042115 (4 pages).
International Preliminary Report on Patentability dated Aug. 26, 2008 for PCT/US2006/045151.
International Search Report dated Jun. 2, 2004 for PCT/US2003/037946 (3 pgs.).
International Search Report and Written Opinion dated Jun. 17, 2005 for PCT/US2004/012672 (5 pgs.).
International Search Report and Written Opinion dated Aug. 6, 2008 for PCT/US2006/045151 (16 pgs.).
International Search Report and Written Opinion dated Nov. 26, 2007 for International Appln. No. PCT/US07/070304 (9 pgs.).
International Preliminary Report on Patentability dated Jun. 25, 2006 for International Application No. PCT/US2004/012672 (4 pgs.).
International Preliminary Report on Patentability dated Apr. 13, 2005 for International Application No. PCT/US2003/037946 (4 pgs.).
U.S. Appl. No. 60/460,678, filed Apr. 4, 2003 (30 pgs.).
Abidi, S.M. Abbas et al., "Differential Influence of Antiestrogens on the in vitro Release of Gelatinases (type IV Collagenases) by Invasive and Non-invasive breast cancer cells", *Clinical and Experimental Metastasis*, vol. 15, No. 4, pp. 432-439, 1997.
Akahoshi et al., "Expression of Monocyte Chemotactic and Activating Factor in Rheumatoid Arthritis," *Arthritis Rheum.*, 36:762-771 (1993).
Alam et al., "Monocyte Chemotactic and Activating Factor Is a Potent Histamine-releasing Factor for Basophils," *J. Clin. Invest.*, 89:723-728 (1992).
Allavena et al., "Induction of natural killer cell migration by monocyte chemotactic protein-1, -2 and -3", *Eur. J. Immunol.*, 24:3233-3236 (1994).
Aukrust et al., "Elevated Circulating Levels of C-C chemokines in Patients With Congestive Heart Failure", *Circulation*, 97:1136-1143 (1998).
Baggiolini et al., "Interleukin-8 and Related Chemotactic Cytokines-CXC and CC Chemokines", *Adv. Immunol.*, 55:97-179 1994.
Baselga et al., "Phase II Study of weekly intravenous recombinant humanized anti-p185 Her2 monoclonal antibody in patients with HER2/neu-overexpressing metastic breast cancer", *J. of Clin. Oncol.* 14(3): 737-744, Mar. 1996.
Benz et al., "Estrogen-Dependent, Tamoxifen-Resistant Tumorigenic Growth of MCF-7 Cells Transfected with HER2/*neu*", *Breast Cancer Research and Treatment*, 24: 85-95 (1992).
Bischoff et al., "Monocyte Chemotactic Protein 1 Is a Potent Activator of Human Basophils", *J. Exp. Med.*, 175:1271-1275 (1992).
Blobel et al., "Adams: Key Components in EGFR Signalling and Development", *Nature*, 6: 32-43 (2005).
Boring et al., "Impaired Monocyte Migration and Reduced Type 1 (TI 1) Cytokine Responses in C-C Chemokine Receptor 2 Knockout Mice," *J. Clin. Invest.*, 100:2552-2561 (1997).
Boring et al., "Decreased lesion formation in CCR2 mice reveals a role for chemokines in the initiation of atherosclerosis", *Nature*, 394:894-897 (1998).
Brodmerkel, C. M., et al., "Discovery and Pharmacological Characterization of a Novel Rodent-Active CCR2 Antagonist, INCB3344", *J. Immunol.* 2005, 175(8), 5370-8.
Brown, P.D., "Ongoing Trials with Matrix Metalloproteinase Inhibitors", *Expert Opinion on Investigational Drugs*, vol. 9 No. 9, pp. 2167-2177, 2000.

Burns et al., "Conversion of an MMP-potent scaffold to an MMP-selective HER-2 sheddase inhibitor via scaffold hybridization and subtle P'$_1$ permutations", *Bioorganic & Medicinal Chemistry Letters* 18 (2008) 560-564.

Butcher, "Leucocyte-Endothelial Cell Recognition: Three (or more) Steps to Specificity and Diversity", *Cell* 67:1033-1036 1991.

Carr et al., "Monocyte chemoattractant protein 1 acts as a T-lymphocyte chemoattractant", *Proc. Natl. Acad. Sci. USA*, 91:3652-3656 (1994).

Chang, C and Werb, Z., "The Many Faces of Metalloproteases: Cell Growth, Invasion, Angiogenesis and Metastasis", *Trends in Cell Biology*, 11(11): S37-S43 2001.

Charo et al., "Molecular cloning and functional expression of two monocyte chemoattractant protein 1 receptors reveals alternative splicing of the carboxyl-terminal tails", *Proc. Natl. Acad. Sci. USA*, 91:2752-2756 (1994).

Chemical Encyclopedic Dictionary, I.L. Knunyants, ed. "Sovetskaya Entsiklopedia", Moscow, 1983, 130-131 (terms Getianks-Hydrogenolysis); (translated).

Collins et al., "Molecular Rearrangements. XX.III. The Mechanism of Hydride Shift during Hydrolyses of Certain Substituted Norbornyl Tosylates", *J. Am. Chem. Soc.* 89:1652-1661 1967.

Collins et al., "Molecular Rearrangements. XXIX. Exo/Endo Stereospecificity of Substituted Classical Norbernyl Cations. A Reassessment of "Hot" Carbonium Ions", *J. Org. Chem.* 37:4358-4366 (1972).

Combadiere et al., "Cloning and Functional Expression of a Human Eosinophil CC Chemokine Receptor", *J Biol. Chem.*, 270:16491-16494 (1995).

Conti et al., "Will MCP-1 and RANTES Take Center Stage in Inflammatory Diseases Including Asthma?" *Allergy and Asthma Proc.*, 19:121-123 (1998).

Dowsett et al., "HER-2 Amplification Impedes the Antiproliferative Effects of Hormone Therapy in Estrogen Receptor-Positive Primary Breast Cancer", *Cancer Research*, 61: 8452-8458 (2001).

Fridman et al. "Preclinical characterization of INCB7839, a potent and selective inhibitor of ErbB ligand and HER2 receptor shedding: inhibition of ADAM 10 and ADAM 17 for the treatment of breast cancer", *30$^{th}$ Annual San Antonio Breast Cancer Symposium*, Dec. 13-16, 2007 (1 pg.).

Gao et al., "Impaired Host Defense, Hematopoiesis, Granulomatous Inflammation and Type 1-Type 2 Cytokine Balance in Mice Lacking CC Chemokine Receptor 1", *J. Exp. Med.*, 185:1959-1968 (1997).

Gerard et al., "Targeted Disruption of the β-Chemokine Receptor CCRI Protects against Pancreatitis-associated Lung Injury," *J. Clin. Invest.*, 100:2022-2027 (1997).

Gesualdo et al., "Monocyte recruitment in cryoglobulinemic membranoproliferative glomerulonephritis: A pathogenetic role for monocyte chemotactic peptide-1", *Kidney Int.*, 51:155-163 (1997).

Gillitzer et al., "MCP-1 mRNA Expression in Basal Keratinocytes of Psoriatic Lesions", *J. Invest. Dermatol.*, 101:127-131 (1993).

Gong, "An Antagonist of Monocyte Chemoattractant Protein 1 (MCP-1) Inhibits Arthritis in the MRL-*lpr* Mouse Model", *J. Exp. Med.*, 186:131-137 (1997).

Gonzalo et al., "The Coordinated Action of CC Chemokines in the Lung Orchestrates Allergic Inflammation and Airway Hyper-responsiveness", *J. Exp. Med.*, 188:157-167 (1998).

Grimm et al., "Enhanced expression and production of monocyte Chemoattractant protein-1 in inflammatory bowel disease mucosa", *J. Leukoc. Biol.*, 59:804-812 (1996).

Gu et al., "Absence of Monocyte Chemoattractant Protein-1 Reduces Atherosclerosis in Low Density Lipoprotein Receptor-Deficient Mice", *Mol, Cell*, 2:275-281 (1998).

Guzman et al., "Monocyte Chemotactic Protein Antibody Inhibits Restenosis in the Rabbit Atherosclerotic Model", abstract, *Abstracts from the 66$^{th}$ Scientific Sessions Georgia World Congress Center*, Atlanta, Georgia. Nov. 8-11, Circulation, 1993, 88 (suppl.), 1-371.

Hayes et al., "Human Vascular Smooth Muscle Cells Express Receptors for CC Chemokines", *Arterioscler. Thromb. Vasc. Biol.*, 18:397-403 (1998).

Hensley, G. C., et al., "Synthesis and Biological Activity of Some 1-Substituted 3-Pyrrolidinylureas", *J. Med. Chem.* (1968), 11, 1034-1037.

Hesselgesser et al., "Identification and Characterization of Small Molecule Functional Antagonists of the CCR1 Chemokine Receptor", *J Biol. Chem.*, 273(25):15687-15692 (1998).

Holgate, "Release of RANTES, MIP-1α, and MCP-1 into Asthmatic Airways Following Endobronchial Allergen Challenge", *Am. J. Respir. Crit. Care Med.*, 156:1377-1383 (1997).

Holmes et al., "Structure and Functional Expression of a Human Interleukin-8 Receptor", *Science*, 253:1278-1280 (1991).

Horuk, "Molecular properties of the chemokine receptor family", *Trends Pharm. Sci.*, 15:159-165 (1994).

Hynes, N. and Lane, H., "ERBB Receptors and Cancer: The Complexity of Targeted Inhibitors", *Nature Reviews*, 5:341-354 (2005).

Infante et al., "A multicenter phase Ib study of the safety, pharamacokinetics, biological activity and clinical efficacy of INCB7839, a potent and selective inhibitor of ADAM 10 and ADAM17", *30$^{th}$ Annual San Antonio Breast Cancer Symposium*, Dec. 13-16, 2007 (1 pg.).

Jahnz-Rozyk et al., "Monocyte chemotactic and activating factor/monocyte chemoattractant protein (MCAF/MCP-1) in bronchoalveolar lavage fluid from patients with atopic asthma and chronic bronchitis", *J. Invest. Allergol. Clin. Immunol.*, 7(4):254-259 (1997).

Jiang et al., "Monocyte Chemoattractant Protein-1 Regulates Adhesion Molecule Expression and Cytokine Production in Human Monocytes", *J. Immunol.*, 148:2423-2428 (1992).

Jolicoeur et al., "Increased Expression of Monocyte Chemotactic Protein-1 in the Endometrium of Women with Endometriosis", *Am. J. Pathol.*, 152:125-133 (1998).

Karpus et al., "MIP-1α and MCP-1 differentially regulate acute and relapsing autoimmune encephalomyelitis as well as Th1/Th2 lymphocyte differentiation", *J. Leukoc. Biol.*, 62:681-687 (1997).

Kaudewitz et al, 1986, "Atypical Cells in Lymphomatoid Papulosis Express the Hodgkin Cell-Associated Antigen Ki-1", *J. Invest. Dermatol.*, 86:350-354.

Kimura et al., "Alleviation of Monocrotaline-Induced Pulmonary Hypertension by Antibodies to Monocyte Chemotactic and Activating Factor/Monocyte Chemoattractant Protein-1", *Lab. Invest.*, 79(5):571-581 (1998).

Koch et al., "Enhanced Production of Monocyte Chemoattractant Protein-1in Rheumatoid Arthritis", *J. Clin. Invest.*, 90:772-779 (1992).

Kuna et al., "Monocyte Chemotactic and Activating Factor Is a Potent Histamine-releasing Factor for Human Basophils", *J. Exp. Med.*, 175:489-493 (1992).

Kurihara et al., "Defects in Macrophage Recruitment and Host Defense in Mice Lacking the CCR2 Chemokine Receptor", *J. Exp. Med.*, 196(10):1757-1762 (1997).

Kurokawa H. and Arteaga C., "ErgB (HER) Receptors Can Abrogate Antiestrogen Action in Human Breast Cancer by Multiple Signaling Mechanisms", *Clinical Cancer Research*, 9:511s-515s (2003).

Kurokawa H. and Arteaga C., "Inhibition of erbB Receptor (HER) Tyrosine Kinases as a Strategy to Abrogate Antiestrogen Resistance in Human Breast Cancer", *Clinical Cancer Research*, 7: 4436s-4442s (Suppl.) (2001).

Kurokawa et al., "Inhibition of HER2/neu (erbB-2) and Mitogen-Activated Protein Kinase Enhances Tamoxifen Action Against HER2-Overexpressing, Tamoxifen-Resistant Breast Cancer Cells", *Cancer Research*, 60: 5887-5894 (2000).

Kuziel et al., "Severe reduction in leukocyte adhesion and monocyte extravasation in mice deficient in CC chemokine receptor 2", *Proc. Natl. Acad. Sci.*, USA, 94:12053-12058 (1997).

Lahrtz et al., "Chemotactic activity on mononuclear cells in the cerebrospinal fluid of patients with viral meningitis is mediated by interferon-γ inducible protein-10 and monocyte chemotactic protein-1", *Eur. J. Immunol.*, 27:2484-2489 (1997).

Lawrence and Springer, "Leukocytes Roll on a Selectin at Physiologic Flow Rates: Distinction from and Prerequisite for Adhesion through Integrins", *Cell* 65:859-873 1991.

Lipton et al., "Serum HER-2/neu and Response to the Aromatase Inhibitor Letrozole Versus Tamoxifen", *Journal of Clinical Oncology*, 21(10), 1967-1972 (2003).

Liu et al., "Inhibition of HER-2/*neu* Kinase Impairs Androgen receptor Recruitment to the Androgen Responsive Enhancer", *Cancer Res.*, 65(8); 3404-3409 (2005).

Liu, X. et al. "Selective inhibition of ADAM metalloproteases blocks Her-2 extracellular domain (ECD) cleavage and potentiates trastuzumab in blocking the growth of Her-2 overexpressing breast cancer cells", Poster/Abst #6051, *28th Annual San Antonio Breast Cancer Symposium*, Dec. 8-11, 2005, San Antonio, TX (1 pg.).

Liu X. et al. "INCB3619, a Novel Potent and Selective ADAM Protease Inhibitor, Blocks HER-2 Extracellular Domain (ECD) Shedding and Enhances Antitumor Activities of Trastuzumab", Poster #B193, *San Antonio Breast Cancer Symposium*, Dec. 2005 (1 pg.).

Lloyd et al., "RANTES and Monocyte Chemoattractant Protein-1 (MCP-1) Play an Important Role in the Inflammatory Phase of Crescentic Nephritis, but Only MCP-1 Is Involved in Crescent Formation and Interstitial Fibrosis", *J. Exp. Med.*, 185:1371-1380 (1997).

Lloyd et al., "The role of chemokines in tissue inflammation and autoimmunity in renal diseases", *Curr. Opin. Nephrol. Hypertens.*, 7:281-287 (1998).

Loetscher et al., "Monocyte chemotactic proteins MCP-1, MCP-2, and MCP-3 are major attractants for human $CD4^+$ and $CD8^+$ T lymphocytes", *FASEB J.*, 8:1055-1060 (1994).

Loetscher et al., "Activation of NK Cells by CC Chemokines", *J. Immunol.*, 156:322-327 (1996).

Lu et al., "Abnormalities in Monocyte Recruitment and Cytokine Expression in Monocyte Chemoattractant Protein 1-deficient Mice", *J. Exp. Med.*, 187:601-608 (1998).

Lucchesini et al., "Synthesis of 4-Unsubstituted Isothiazoles", *Heterocycles*, 29:97-102 (1989).

Lukacs, "Differential Recruitment of Leukocyte Populations and Alteration of Airway Hyperreactivity by C-C Family Chemokines in Allergic Airway Inflammation", *J. Immunol.*, 158:4398-4404 (1997).

Luster, "Chemokines—Chemotactic Cytokines that Mediate Inflammation", *New Eng. J Med.*, 338:436-445 (1998).

MacDermott et al., "The Central Role of Chemokines (Chemotactic Cytokines) in the Immunopathogenesis of Ulcerative Colitis and Crohn's Disease", *Inflammatory Bowel Diseases*, 4(1):54-67 (1998).

Marra et al., "Increased Expression of Monocyte Chemotactic Protein-1 during Active Hepatic Fibrogenesis", *Am. J. Pathol.*, 152:423-430 (1998).

Marson, L.P. et al., "Angiogenesis and Breast Cancer", *The Breast,*; vol. 7, No. 6, pp. 299-307, 1998.

Massarweh et al., "Mechanisms of Tumor Regression and Resistance to Estrogen Deprivation and Fulvestrant in a Model of Estrogen Receptor-Positive, HER-2/*neu*-Positive Breast Cancer", *Cancer Res.*, 66(16): 8266-8273 (2006).

Matsushima et al., "Purification and characterization of a novel monocyte chemotactic and activating factor produced by a human myelomonocytic cell line", *J. Exp. Med.*, 169:1485-1490 (1989).

McManus et al., "MCP-1, MCP-2 and MCP-3 expression in multiple sclerosis lesions: an immunohistochemical and in situ hybridization study", *J. Neuroimmunol.* 86:20-29 (1998).

Mellinghoff et al., HER2.neu Kinase-Dependent Modulation of Androgen Receptor Function Through Effects on DNA Binding and Stability, *Cancer Cell* 6: 517-527 (2004).

Miller et al., "Emergence of MCF-7 Cells Overexpressing a Transfected Epidermal Growth Factor Receptor (EGFR) Under Estrogen-Depleted Conditions: Evidence for a Role of EGFR in Breast Cancer Growth and Progression", *Cell Growth & Differentiation*, 5:1263-1274 (1994).

Moss, M. and Lambert, M., "Shedding of Membrane Proteins by ADAm Family Proteases", *Essays in Biochemistry*, The Biochemical Society, London; pp. 141-153 (2002).

Murphy et al., "Cloning of complementary DNA encoding a functional human interleukin-8 receptor", *Science*, 253:1280-1283 (1991).

Murphy, "The molecular biology of leukocyte chemoattractant receptors", *Ann. Rev. Immunol.*, 12:593-633 (1994).

Nelken et al., "Monocyte chemoattractant protein-1 in human atheromatous plaques", *J. Clin. Invest.*, 88:1121-1127 (1991).

Neote et al., "Molecular cloning, functional expression, and signaling characteristics of a C-C Chemokine receptor", *Cell*, 72:415-425 (1993).

Newby et al., "Expression of Epidermal Growth Factor Receptor and c-erbB2 During the Development of Tamoxifen Resistance in Human Breast Cancer", *Clinical Cancer Research*, 3:1643-1651 (1997).

Noris et al., "Monocyte chemoattractant protein-1 is excreted in excessive amounts in the urine of patients with lupus nephritis", *Lab. Invest.*, 73(6):804-809 (1995).

Ogata et al., "The role of monocyte chemoattractant protein-1 (MCP-1) in the pathogenesis of collagen-induced arthritis in rats", *J. Pathol.*, 182:106-114 (1997).

Oppenheim et al., "Properties of the novel proinflammatory supergene "intercrine" cytokine family", *Annu. Rev. Immunol.*, 9:617-648 (1991).

Osborne et al., "Upregulation of Estradiol C16α-hydorxylation in Human Breast Tissue: A Potential Biomarker of Breast Cancer Risk", *Journal of the National Cancer Institute*, 85(23): 1917-1920.

Parikh et al., "Development of a Sustained Release Formulation for a Novel Anti-Cancer Agent", Poster #T3378 (Nov. 2007) (1 pg.).

Pharmaceutical Drugs (Guide for Physicians) Part I, $12^{th}$ ed. M.S. Mashkovskiy, ed., "Meditsina," Moscow, 1993, p. 8 (2 pgs.).

Povarny et al., "Stereo- and regioselective oxymercuration—demercuration of bicycle [3.2.1 ]oct-2- ene skeleton", *Tetrahedron Lett.*, 25(12):1311-1312 (1984).

Power et al., "Molecular cloning and functional expression of a novel CC Chemokine receptor cDNA from a human basophilic cell line", *J. Biol. Chem.*, 270:19495-19500 (1995).

Rand et al., "Inhibition of T cell recruitment and cutaneous delayed-type hypersensitivity-induced inflammation with antibodies to monocyte chemoattractant protein-1", *Am. J. Pathol.*, 148(3):855-864 (1996).

Ransohoff et al., "Do chemokines mediate leukocyte recruitment in post-traumatic CNS inflammation?", *Trends Neurosci.*, 21:154-159 (1998).

Razandi, M. et al., "Proximal Events in Signaling by Plasma Membrane Estrogen Receptors", *The Journal of Biological Chemistry*, vol. 278, No. 4, pp. 2701-2712, 2003.

Rau, K.M, et al., "The Mechanisms and Managements of Hormone-Therapy Resistance in Breast and Prostate Cancers", Endocrine-Related Cancer, vol. 12. No. 3, pp. 511-532, 2005.

Reinecker et al., "Monocyte-chemoattractant protein 1 gene expression in intestinal epithelial cells and inflammatory bowel disease mucosa", *Gastroenterology*, 108:40-50 (1995).

Rbbinson et al., "Chemokine expression in rheumatoid arthritis (RA): evidence of RANTES and macrophage inflammatory protein (MIP)-1β production by synovial T cells", *Clin. Exp. Immunol.*, 101:398-407 (1995).

Robinson et al., "A Chemokine Receptor Antagonist Inhibits Experimental Breast Tumor Growth", *Cancer Research*, 63:8360-8365 (2003).

Rollins et al., "Recombinant human MCP-1/JE induces chemotaxis, calcium flux, and the respiratory burst in human monocytes", *Blood*, 78:1112-1116 (1991).

Rollins et al., "Cloning and expression of *JE*, a gene inducible by platelet-derived growth factor and whose product has cytokine-like properties", *Proc. Natl. Acad. Sci.*, USA 85:3738-3742 (1988).

Rollins, "Chemokines", *Blood*, 90:909-928 (1997).

Rosen et al., "Design, synthesis, and properties of (4S)-7-(4-Amino-2-substituted-pyrrolidin-1-yl)quinolone-3-carboxylic acids", *J. Med. Chem.*, 31:1598-1611 (1988).

Ravin et al., "Chemotactic factors and renal inflammation", *Am. J. Kidney. Dis.*, 31(6):1065-1084 (1998).

Sabnis et al., "The Role of Growth Factor Receptor in Human Breast Cancer Cells Adapted to Long-Term Estrogen Deprivation", *Cancer Res..* 65(9): 3903-3910 (2005).

Scatena, R., "Prinomastat, A Hydroxamate-Based Matrix Metalloproteinase Inhibitor. A Novel Pharmacological Approach for Tissue Remodelling-Related Diseases", *Expert Opinion on Investigational Drugs*, vol. 9, No. 9, .2159-2165, 2000.

Saitoh et al., "Urinary levels of monocyte chemoattractant protein (MCP)-1 and disease activity in patients with IgA nephropathy", *J. Clin. Lab. Anal.*, 12:1-5 (1998).

Salkowski et al., "Pulmonary and hepatic gene expression following cecal ligation and puncture: monophosphoryl lipid A prophylaxis attenuates sepsis-induced cytokine and chemokine expression and neutrophil infiltration", *Infect. Immun.*, 66(8):3569-3578 (1998).

Samson et al., "Molecular cloning and functional expression of a new human CC-Chemokine receptor gene" *Biochemistry*, 35:3362-3367 (1996).

Sandosham et al., "Stannylation in the electrophilic 2- and 4/6-pyrimidine position and the use of stannylpyrimidines in coupling and tin-lithium exchange reations", *Tetrahedron*, 50:275-284 (1994).

Schall and Bacon, "Chemokines, leukocyte trafficking, and inflammation", *Curr. Opin. Immunol.*, 6:865-873 (1994).

Schiff R. and Osborne C.K., "New Insight Into Estrogen Receptor-α-Function and Its Implication for Endocrine Therapy Resistance in Breast Cancer", *Breast Cancer Research*, 7: 205-211 (2005).

Schimmer et al., "Streptococcal cell wall-induced arthritis: requirements for IL-1, IL-10, IFN-γ, and monocyte chemoattractant protein-1", *J. Immunol.*, 160:1466-1471 (1998).

Schrier et al., "Role of chemokines and cytokines in a reactivation model of arthritis in rats induced by injection with streptococcal cell walls", *J. Leukoc. Biol.*, 63(3):359 (1998).

Seals D. and Courtneidge S., "The ADAMs Family of Metalloproteases: Multidomain Proteins with Multiple Functions", *Genes & Development*, 17:7-30 (2003).

Sefton, 1989, "Implantable Pumps", *CRC Crit. Ref. Biomed. Eng.*, 14:201.

Seino et al., "Expression of leukocyte chemotactic cytokines in myocardial tissue", *Cytokine*, 7(3):301-304 (1995).

Shepherd et al., "Targeted therapy for lung cancer at the clinical level", *Proceedings of the American Association of Cancer Research Annual Meeting*, 43: 1167 and 1168, Mar. 2002.

Shin et al., "Pharmacological characterization of INCB3344, a small molecule antagonist of human CCR2", *Biochemical and Biophysical Research Communications* 387, (2009) 251-255.

Sousa et al., "Increased expression of the monocyte chemoattractant protein-1 in bronchial tissue from asthmatic subjects", *Am. J. Respir., Cell Mol. Biol.*, 10:142-147 (1994).

Springer, "Adhesion receptors of the immune system", *Nature*, 346:425-434 (1990).

Stabile et al., "Combined Targeting of the Estrogen Receptor and the Epidermal Growth Factor Receptor in Non-Small Cell Lung Cancer Shows Enhanced Antiproliferative Effects", *Cancer Res.*, 65(4): 1459-1651 (2005).

Sugiyama et al., "Chemokines in the bronchoalveolar lavage fluid of patients with sarcoidosis", *Internal Medicine*, 36:856-860 (1997).

Takeya et al., "Detection of monocyte chemoattractant protein-1 in human atherosclerotic lesions by an anti-monocyte chemoattractant protein-1 monoclonal antibody", *Hum. Pathol.*, 24:534-539 (1993).

Vaddi et al., "Regulation of monocyte integrin expression by β-familychemokines," *J. Immunol.*, 153:4721-4732 (1994).

Valente et al., "Purification of a monocyte chemotatic factor secreted by nonhuman primate vascular cells in culture", *Biochemistry*, 27:4162-4168 (1998).

Van Agthoven et al., "Ectopic Expression of Epidermal Growth Factor Receptors Induces Hormone Independence in ZR=75-1 Human Breast Cancer Cells", *Cancer Research* 52:5082-5088 (1992).

Wada et al., "Monitoring urinary levels of monocyte chemotactic and activating factor reflects disease activity of lupus nephritis", *Kidney Int.*, 49:761-767 (1996).

Wada et al., Intervention of crescentic glomerulonephritis by antibodies to monocyte chemotactic and activating factor (MCAF/MCP-1), *FASEB J.*, 10:1418-1425 (1996).

Wang et al., "Synthesis of 2-substituted (±)-(2R,3R,5R)-Tetrahydrofuran-3,5-dicarboxylic acid derivatives", *J. Org. Chem.*, 66:2052-2056 (2001).

Weisberg, S. P., et al., "CCR2 modulates inflammatory and metabolic effects of high-fat feeding.", *J. Clin. Invest.*, (2006) 116(1), 115-24; Epub, Dec. 8, 2005.

Wong et al., "Evidence for RANTES, monocyte chemotactic protein-1, and macrophage inflammatory protein-1β expression in Kawasaki disease", *J. Rheumatol.*, 24:1179-1185 (1997).

Wright et al., "Expression of c-*erbB*-2 Oncoprotein: a prognostic Indicator in Human Breast Cancer", *Cancer Research*, 49: 2087-2090 (1989).

Xue et al., "Cyclic hydroxamic acids as metalloproteinase inhibitors", abstract for International Publication No. WO9965867, CAS132:49888 (2 pgs.).

Yamagami et al., "cDNA cloning and functional expression of a human monocyte chemoattractant protein I receptor", *Biochem. Biophys. Res. Commun.*, 202(2):1156-1162 (1994).

Yao et al., "Design and identification of selective HER-2 sheddase inhibitors via P1' manipulation and unconventional P2' perturbations to induce a molecular metamorphoses", *Bioorganic & Medicinal Chemistry Letters*, 18 (2008) 159-163.

Yla-Herttuala et al., "Expression of monocyte chemoattractant protein 1 in macrophage-rich areas of human and rabbit atherosclerotic lesions", *Proc. Nad. Acad. Sci. USA*, 88:5252-5256 (1991).

Yokoyama et al., "Urinary levels of chemokines (MCAF/MCP, IL-8) reflect distinct disease activities and phases of human IgA nephropathy", *J. Leukoc. Biol.*, 63(4):493-499 (1998).

Yoshimura et al., "Purification and amino acid analysis of two human monocyte chemoattractants produced by phytohemagglutinin-stimulated human blood mononuclear leukocytes", *J. Immunol.*, 142:1956-1962 (1989).

Zeyneloglu et al., "The effect of monocyte chemotactic protein 1 in intraperitoneal adhesion formation in a mouse model", *Am. J. Obstet. Gynecol.*, 179:438-443 (1998).

Zeyneloglu et al., "The role of monocyte chemotactic protein-1 in intraperitoneal adhesion formation", Human Reproduction, 13(5):1194-1199 (1998).

Zheng, C.J. et al., "Trends in Exploration of Therapeutic Targets", *Drug News and Perspectives*,vol. 18, No. 2, . 109-127, 2005.

Drummond, AH et al. "Preclinical and Clinical Studies of MMP Inhibitors in Cancer", *Annals of the New York Academy of Sciences*, 878: 228-235 (1999).

Miller KD et al., "A Randomized Phase II Feasibility Trial of BMS-275291 in Patients with Early Stage Breast Cancer", *Clinical Cancer Research*, 10: 1971-1975 (2004).

Fridman, JS et al. "Selective Inhibition of ADAM Metalloproteases as a Novel Approach for Modulating ErbB Pathways in Cancer", Clinical Cancer Research, 13: 1892-1902 (2007).

U.S. Adopted Name: Aderbasib; Chemical Compound Formula: C21H28N4O5; Molecular Weight: 416.47; Compound Name: (6S,78)-; (2) Methyl (6S,7S)-7-[(hydroxyamino)carbanyl]-6-[(4-phenylpiperazin-1-yl)carbonyl]-5-azaspiro[2.5]octane-5-carboxylate; CAS#791828-58-5; Antineoplastic; ErbB Sheddase (ADAM) Inhibitor. INCB 007839 *Pharmacopeial Forum*, 34: 1642 (Nov.-Dec. 2008).

Wall, et al., "A phase I and pharmacological study of the matrix metalloproteinase inhibitor BB-3644 in patients with solid tumours", *British J. Cancer*, 90:800-804 (2004).

Coussens, et al., "Matrix Metalloproteinase Inhibitors and Cancer-Trials and Tribulations", 295:2387-92 (2002).

\* cited by examiner

SHEDDASE INHIBITORS COMBINED WITH CD30-BINDING IMMUNOTHERAPEUTICS FOR THE TREATMENT OF CD30 POSITIVE DISEASES

CROSS REFERENCE TO RELATED APPLICATIONS

This application claims the benefit of U.S. Provisional Ser. No. 60/811,308, filed Jun. 5, 2006, the disclosure of which is incorporated herein by reference in its entirety.

FIELD OF THE INVENTION

The present invention is directed to pharmaceutical methods of treating CD30 positive diseases, such as Hodgkin's disease, by administering to a patient a combination of sheddase inhibitor and anti-CD30 immunotherapeutic.

BACKGROUND OF THE INVENTION

CD30 is a 105-120 kDa integral membrane glycoprotein and a member of the tumor necrosis factor receptor (TNF-R) superfamily. Under normal conditions expression of CD30 is restricted to activated T and B cells and absent from resting lymphocytes, resting monocytes and from normal cells outside of the immune system. CD30 expression in tissues where it is normally absent has been linked to several disease states. Originally identified on Reed-Sternberg cells in Hodgkin's disease (HD or Hodgkin's lymphoma) using the Ki-1 monoclonal antibody (mAb) (Stein et al., 1985, Blood, 66, 848-858; Laudewitz et al, 1986, J. Invest. Dermatol. 86:350-354), CD30 has also been shown to be expressed on a subset of non-Hodgkin's lymphomas (NHL), including Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), and entroblastic/centrocytic (cb/cc) follicular lymphomas (Stein et al., Blood 66:848 (1985); Miettinen, Arch. Pathol. Lab. Med. 116:1197 (1992); Piris et al., Histopathology 17:211 (1990); Bums et al., Am. J. Clin. Pathol. 93:327(1990); and Eckert et al., Am. J. Dermatopathol. 11:345 (1989)), as well as several virally-transformed lines such as human T-Cell Lymphotrophic Virus I or II transformed T-cells, and Epstein-Barr Virus transformed B-cells (Stein et al., Blood 66:848 (1985); Andreesen et al., Blood 63:1299 (1984)). In addition, CD30 expression has been documented in embryonal carcinomas, nonembryonal carcinomas, malignant melanomas, mesenchymal tumors, and myeloid cell lines and macrophages at late stages of differentiation (Schwarting et al., Blood 74:1678 (1989); Pallesen et al., Am J. Pathol. 133:446 (1988); Mechtersheimer et al., Cancer 66:1732 (1990); Andreesen et al., Am. J. Pathol. 134:187 (1989)). CD30 is also expressed at high levels by activated cells in autoimmune disease.

The percentage of CD30 positive cells in normal individuals is relatively small, rendering CD30 an ideal marker of disease and target for antibody-mediated therapy. Accordingly, CD30 is widely used as a clinical marker and therapeutic target for Hodgkin's disease (HD). Monoclonal antibodies specific for the CD30 antigen have been explored as vehicles for the delivery of cytostatic drugs, plant toxins and radioisotopes in both pre-clinical models and clinical studies (Engert et al., 1990, Cancer Research 50:84-88; Barth et al., 2000, Blood 95:3909-3914). In patients with HD, targeting of the CD30 antigen was achieved with low doses of the anti-CD30 mAb, BerH2 (Falini et al., 1992, British Journal of Haematology 82:38-45). In a subsequent clinical trial, a toxin (saporin) was chemically conjugated to the antibody BerH2 and all four patients demonstrated reductions in tumor mass (Falini et al., 1992, Lancet 339:1195-1196). Similarly, anti-CD30 antibodies conjugated with deglycosylated ricin A-chain toxin were found effective in inhibiting the progression of Hodgkin's disease (Schnell, R. et al. 2003, Annals of Oncology, 14, 729). Anti-CD30 antibodies, their conjugates, and corresponding immunotherapic methods are further reported in U.S. Pat. App. Pub. Nos. 2005/0123536, 2004/0018194, and 2004/0006215; as well as WO 2006/039644, WO 2005/001038, and WO 2003/043661. Despite the initial promising results, liver toxicity and vascular leak syndrome associated with immunotoxin therapy potentially limits the ability to deliver curative doses of these agents (Tsutsumi et al., 2000, Proc. Nat'l Acad. Sci. U.S.A. 97:8545-8553).

CD30 is endoproteolytically cleaved to form circulating, soluble protein. Soluble CD30 (sCD30) is detectable in the circulation of patients suffering from diseases including rheumatoid arthritis (Gerli et al., 2000, J. Immunol. 164, 4399-4407), multiple sclerosis (McMillan et al. 2000, Acta Neurol. Scand. 101 :239-243) and systemic sclerosis (Ihn et al., J. Rheumatol. 27:698-702). Serum level of sCD30 in patients suffering from Hodgkin's disease (HD) was found to be a prognostic indicator of the disease (Nadali, G. et al. 1998, Blood. 91(8), 3011), and shedding of CD30 has also been detected in anaplastic large-cell lymphoma (ALCL) as well as adult T-cell leukemia (ATL). Shedding of CD30 is mediated by the metalloprotease TACE (ADAM17) (Hansen, H. P. et al. 2000, J. of Immunol. 6704-6709).

It has been postulated that shedding of the CD30 extracellular antigen domain inhibits the effectiveness of immunotherapy and contributes to side effects such as organ toxicity and vascular leak syndrome. In one preclinical rodent study, anti-CD30 immunotoxins were administered concomitantly with the hydroxamate metalloprotease inhibitor BB-3644 (Matthey, B. et al., 2004, Int. J. Cancer, 111, 568). It was found that the combination was substantially more effective both in vitro and in vivo than treatment with immunotoxin alone. An earlier in vitro study along the same lines had similar results (Hansen et al., 2002, Int. J. Cancer, 98, 210).

In view of the above findings, there is a continuing need to improve the effectiveness of immunotherapy in connection with CD30 positive diseases. The methods and compositions herein related to combinations of immunotherapeutics with sheddase inhibitors help provide for this ongoing need.

SUMMARY OF THE INVENTION

The present invention provides methods of treating a disease in a patient, such as a disease that is characterized by expression of CD30, comprising administering to said patient:

i) an antibody or antibody-conjugate which binds CD30; and ii) a CD30 sheddase inhibitor such as, for example, a compound of Formula I:

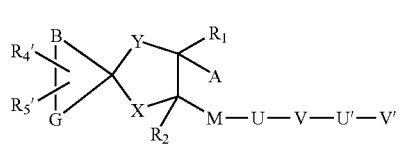

or a pharmaceutically acceptable salt thereof, wherein constituent variables are defined hereinbelow; wherein the amount of said CD30 shessase inhibitor and said antibody or antibody-conjugate together provide a therapeutically effective amount.

The present invention further provides methods of treating a disease in a patient, wherein said disease is characterized by expression of CD30 and CD30 shedding, comprising administering to said patient:

i) an antibody or antibody-conjugate which binds CD30; and ii) methyl(6S,7S)-7-[(hydroxyamino)carbonyl]-6-[(4-phenylpiperazin-1-yl)carbonyl]-5-azaspiro[2.5]octane-5-carboxylate or pharmaceutically acceptable salt thereof, wherein the amount of the antibody or antibody-conjugate and the amount of the compound or pharmaceutically acceptable salt thereof together provide a therapeutically effective amount.

The present invention further provides methods of treating cancer in a patient, comprising administering to said patient:

i) an antibody or antibody-conjugate which binds CD30; and ii) methyl(6S,7S)-7-[(hydroxyamino)carbonyl]-6-[(4-phenylpiperazin-1-yl)carbonyl]-5-azaspiro[2.5]octane-5-carboxylate or pharmaceutically acceptable salt thereof, wherein the amount of the antibody or antibody-conjugate and the amount of the compound or pharmaceutically acceptable salt thereof together provide a therapeutically effective amount.

The present invention further provides compositions comprising:

i) an antibody or antibody-conjugate that binds CD30;

ii) a pharmaceutically acceptable carrier; and iii) a CD30 sheddase inhibitor such as a compound of Formula I, or pharmaceutically acceptable salt thereof.

DETAILED DESCRIPTION

The present invention provides, inter alia, methods of treating diseases which are positive for expression of CD30 by administering a combination of at least one CD30 sheddase inhibitor such as, for example, compounds of Formula I (provided hereinbelow) and at least one antibody or antibody-conjugate that binds to CD30. While not wishing to be bound by theory, it is believed that such combination provides improved treatment over previous immunotherapies because administration of the sheddase inhibitor can inhibit shedding of the CD30 extracellular antigen region thereby allowing the antibody or conjugate thereof to localize at unshed CD30 in the targeted diseased cells.

CD30 Sheddase Inhibitors

Shedding of CD30 is mediated by the metalloprotease ADAM17 (TACE). Accordingly, compounds which are inhibitors of ADAM17 are contemplated as CD30 sheddase inhibitors. Example ADAM17 inhibitors include compounds of Formula I (below), for which the preparation and characterization are described in U.S. Pat. App. Pub. No. 2004/0259896, which is incorporated herein by reference in its entirety. Further example compounds include those described in U.S. Pat. App. Pub. Nos. 2005/0250789 and 2005/0113344, each of which is incorporated herein by reference in its entirety.

Compounds of Formula I are as follows:

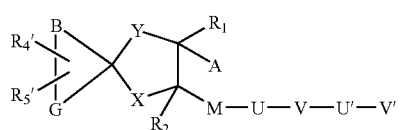

or a pharmaceutically acceptable salt thereof, wherein:

A is $CO_2H$, $C(S)OH$, $C(O)NHOH$, $C(S)NHOH$, $C(O)NHOR_5$, $C(S)NHOR_5$, $N(OH)CHO$, $N(OH)C(O)R_6$, $N(OH)C(S)R_6$, $SH$, $SR_7$ or hydantoinyl;

B and G are independently selected from $(CH_2)_n$, $(CH_2)_nC(O)$, $(CH_2)_nC(S)$, $(CR_dR_f)_nNR_8$, $(CR_dR_f)_nO(CR_dR_f)_r$, $(CR_dR_f)_nS(CR_dR_f)_r$, $OC(O)NR_8$, $OC(S)NR_8$, $O$, $NR_8$, $S(O)_m$, $S$, $C(O)NR_8(CR_dR_f)_n$ and $C(O)(CR_dR_f)_n$;

X and Y are independently selected from absent, $(CH_2)_j$, $C_{1-10}$ alkylene substituted with 0 to 3 $R_a$, $C_{2-10}$ alkenylene substituted with 0, 1 or 2 $R_a$, O, $NR_b$, $S(O)_m$, C=O, $NR_bC(O)$, $NR_bC(O)O$, $NR_bC(O)NR_b$, $C(O)O$, $NR_bS(O)_m$, $NR_bS(O)_mNR_b$ and $(CR_dR_f)_jNR_b$;

M is CO or $S(O)_i$;

U is absent, $C_{1-10}$ alkylene substituted with 0 to 5 $R_a$, $C_{2-10}$ alkenylene substituted with 0 to 2 $R_a$, O, $NR_b$, $NR_bC(O)$, $NR_bC(O)O$, $NR_bC(O)NR_b$, $NR_bS(O)_m$, or $NR_bS(O)NR_b$;

V is absent, $C_{3-13}$ carbocyclyl substituted with 0-5 $R_e$ or heterocyclyl substituted with 0-5 $R_e$;

U' is absent, $C_{1-10}$ alkylene substituted with 0 to 5 $R_a$, $C_{2-10}$ alkenylene substituted with 0 to 2 $R_a$, O, $NR_bS(O)_m$, C=O, $NR_bC(O)$, $NR_bC(O)O$, $NR_bC(O)NR_b$, $C(O)O$, O—($C_{1-10}$ alkylene) or $NR_bS(O)NR_b$;

V' is H, $C_{1-8}$ alkyl, $NR_bR_c$, $C_{3-13}$ carbocyclyl substituted with 0-5 $R_c$ or heterocyclyl substituted with 0-5 $R_e$;

$R_a$ and $R_e$ are independently selected from H, T, $C_{1-8}$ alkylene-T, $C_{2-8}$ alkenylene-T, $C_{2-6}$ alkynylene-T, $C(O)NR_a'(CR_b'R_c')_r$-T, $C(O)O(CR_b'R_c')_r$-T, $S(O)_p(CR_b'R_c')_r$-T, $(CR_b'R_c')_r$—O—$(CR_b'R_c')_r$-T, OH, Cl, F, Br, I, CN, $NO_2$, $NR^IR^{II}$, $COR^{III}$, $COOR^{IV}$, $OR^{IV}$, $CONR^IR^{II}$, $NR^ICONR^IR^{II}$, $OCONR^IR^{II}$, $NR^ICOR^{II}$, $SO_2NR^IR^{II}$, $NR^ISO_2R^{II}$, $NR^ISO_2NR^IR^{II}$, $OSO_2NR^IR^{II}$, $SO_pR^V$, $C_{1-8}$ haloalkyl, $C_{3-13}$ carbocyclyl, heterocyclyl, carbocyclylalkyl, and heterocyclylalkyl, wherein each of said carbocyclyl, heterocyclyl, carbocyclylalkyl, and heterocylcylalkyl groups is optionally substituted by 1, 2, 3, 4, 5 or 6 substituents independently selected from $C_{1-8}$ alkyl, alkoxy, halo, haloalkyl, haloalkoxy, cyano, nitro, amino, alkylamino, dialkylamino, carboxy, carboxy alkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl and arylsufonyl;

$R_b$ and $R_c$ are independently selected from H, T, $C_{1-6}$ alkylene-T, $C_{2-8}$ alkenylene-T, $C_{2-6}$ alkynylene-T, $C(O)NR_a'(CR_c'R_b')_r$-T, $C(O)O(CR_b'R_c')_r$-T, $C(O)(CR_b'R_c')_r$-T, $S(O)_p(CR_b'R_c')_r$-T, $(CR_c'R_b')_r$—O—$(CR_c'R_b')_r$-T, $C(NR_a'R_a')$(=N—CN) and $C(NR_a'R_a')$(=CHNO_2);

$R_d$ and $R_f$ are independently selected from H, $C_{1-6}$ alkyl, $C_{2-6}$ alkenyl, $C_{2-6}$ alkynyl, T, $C_{1-6}$ alkylene-T, $C_{2-8}$ alkenylene-T, $C_{2-6}$ alkynylene-T, $C(O)NR_a'(CR_c'R_b')_r$-T, $C(O)O(CR_b'R_c')_r$-T, $S(O)_p(CR_b'R_c')_r$-T, $(CR_c'R_b')_r$—O—$(CR_c'R_b')_r$-T, OH, Cl, F, Br, I, CN, $N_2$, $NR^IR^{II}$, $COR^{III}$, $COOR^{IV}$, $OR^{IV}$, $CONR^IR^{II}$, $R^INCONR^IR^{II}$, $OCONR^IR^{II}$, $R^INCOR^{II}$, $SO_2NR^IR^{II}$, $NR^ISO_2R^{II}$, $NR^ISO_2NR^IR^{II}$, $OSO_2NR^IR^{II}$, $SO_pR^V$, $C_{1-8}$ haloalkyl, carbocyclyl, heterocyclyl, carbocyclylalkyl, heterocyclylalkyl, carbocyclyloxy, and heterocyclyloxy, wherein each of said carbocyclyl, heterocyclyl, carbocyclylalkyl, heterocyclylalkyl, carbocyclyloxy or heterocyclyloxy groups is optionally substituted by 1, 2, 3, 4, 5 or 6 substituents independently selected from $C_{1-8}$ alkyl, alkoxy, halo, haloalkyl, haloalkoxy, cyano, nitro, amino, alkylamino, dialkylamino, carboxy, carboxy alkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl, and arylsufonyl;

T is H, $C_{1-10}$ alkyl substituted with 0 to 5 $R_b'$, $C_{2-10}$ alkenyl substituted with 0 to 5 $R_b'$, $C_{2-10}$ alkynyl substituted with 0 to 5 $R_b'$, $C_{1-6}$ alkoxy, $C_{3-13}$ carbocyclyl substituted with 0-3 $R_b'$, or heterocyclyl substituted with 0-5 $R_b'$;

$R_a'$, $R_b'$ and $R_c'$ are independently selected from H, $C_{1-6}$ alkyl, $C_{2-6}$ alkenyl, $C_{2-6}$ alkynyl, OH, Cl, F, Br, I, CN, $NO_2$, $NR^I R^{II}$, $COR^{III}$, $COOR^{IV}$, $OR^{IV}$, $CONR^I R^{II}$, $R^I NCONR^I R^{II}$, $OCONR^I R^{II}$, $R^I NCOR^{II}$, $SO_2 NR^I R^{II}$, $NR^I SO_2 R^{II}$, $NR^I SO_2 NR^I R^{II}$, $OSO_2 NR^I R^{II}$, $SO_p R^V$, $C_{1-8}$ haloalkyl, carbocyclyl, heterocyclyl, carbocyclylalkyl, heterocyclylalkyl, carbocyclyloxy, and heterocyclyloxy, wherein each of said carbocyclyl, heterocyclyl, carbocyclylalkyl, heterocyclylalkyl, carbocyclyloxy or heterocyclyloxy groups is optionally substituted by 1, 2, 3, 4, 5, or 6 substituents selected from $C_{1-8}$ alkyl, alkoxy, halo, haloalkyl, haloalkoxy, cyano, nitro, amino, alkylamino, dialkylamino, carboxy, carboxy alkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl or arylsufonyl;

$R_1$ and $R_2$ are independently selected from H, $C_{1-6}$ alkyl, $SR_{10}$, $OR_{10}$ and $NR_{11}R_{12}$;

$R_5$ is H, halogen, T, $C_{1-6}$ alkylene-T, $C_{2-6}$ alkynylene-T, $C(O)NR_a'(CR_c'R_b')_r$-T, $CO(CR_b'R_c')_r$-T, $C(O)O(CR_b'R_c')_r$-T, $S(O)_p(CR_b'R_c')_r$-T, $(CR_b'R_c')_r$—O—$(CR_c'R_b')_r$-T, $NR_{11}R_{12}$, $SR_{18}$ or $OR_{18}$;

$R_4'$ and $R_5'$ are independently selected from H, halogen, T, $C_{1-6}$ alkylene-T, $C_{2-6}$ alkynylene-T, $C(O)NR_a'(CR_c'R_b')_r$-T, $CO(CR_b'R_c')_r$-T, $C(O)O(CR_b'R_c')_r$-T, $S(O)_p(CR_b'R_c')_r$-T, $(CR_c'R_b')_r$—O—$(CR_c'R_b')_r$-T, $NR_{11}R_{12}$, $SR_{18}$, and $OR_{18}$;

or $R_4'$ and $R_5'$ together with the atoms to which they are attached form a ring selected from $C_{3-13}$ carbocyclyl and 3-14 membered heterocyclyl;

$R_6$ and $R_7$ are independently selected from H, $C_{1-6}$ alkyl, $C_{2-8}$ alkenyl and $C_{2-8}$ alkynyl;

$R_8$ is H, $C_{1-10}$ alkylene-T, $C_{2-10}$ alkenylene-T, $C_{2-10}$ alkynylene-T, $(CR_b'R_c')_r O(CR_b'R_c')_r$-T, $(CR_b'R_c')_r NR_a'(CR_b'R_c')_r$-T, $(CR_b'R_c')_r C(O)(CR_b'R_c')_r$-T, $(CR_b'R_c')_r C(O)O(CR_b'R_c')_r$-T, $(CR_b'R_c')_r OC(O)(CR_b'R_c')_r$-T, $(CR_b'R_c')_r C(O)NR_a'(CR_b'R_c')_r$-T, $(CR_b'R_c')_r NR_a'C(O)(CR_b'R_c')_r$-T, $(CR_b'R_c')_r OC(O)O(CR_b'R_c')_r$-T, $(CR_b'R_c')_r OC(O)NR_a'(CR_b'R_c')_r$-T, $(CR_b'R_c')_r NR_a'C(O)O(CR_b'R_c')_r$-T, $(CR_b'R_c')_r NR_a'C(O)NR_a'(CR_b'R_c')_r$-T, $(CR_b'R_c')_r S(O)_p(CR_b'R_c')_r$-T, $(CR_b'R_c')_r SO_2 NR_a'(CR_b'R_c')_r$-T, $(CR_b'R_c')_r NR_a'SO_2(CR_b'R_c')_r$-T, or $(CR_b'R_c')_r SO_2 NR_a'SO_2(CR_b'R_c')_r$-T;

$R_{10}$ is H or $C_{1-6}$ alkyl;

$R_{11}$ and $R_{12}$ are independently selected from H and $C_1$-$C_8$ alkyl;

or $R_{11}$ and $R_{12}$ together with the N atom to which they are attached form a 3-14 member heterocyclic ring;

$R_{18}$ is $C_{1-6}$ alkyl;

$R^I$ and $R^{II}$ are independently selected from H, $C_{1-6}$ alkyl and $C_{3-13}$ carbocyclyl;

$R^{III}$ and $R^{IV}$ are independently selected from H, $C_{1-6}$ alkyl, haloalkyl, carbocyclyl, heterocyclyl, carbocyclylalkyl and heterocyclylalkyl, wherein said carbocyclyl, heterocyclyl, carbocyclylalkyl and heterocyclylalkyl are each optionally substituted by 1, 2, 3, or 4 substituents independently selected from halo, $C_{1-4}$ alkyl and $C_{1-4}$ alkoxy;

$R^V$ is $C_{1-6}$ alkyl, haloalkyl, carbocyclyl or heterocyclyl;

j is 1, 2, 3 or 4;

i is 0, 1 or 2;

n is 0, 1, 2, 3, 4, 5, 6, 7, 8, 9, 10, 11 or 12;

m is 0, 1 or 2;

p is 1 or 2; and r is 0, 1, 2, 3, 4 or 5;

with the provisos:

a) the spiro ring is a stable chemical entity; and b) $NR_g$ and $NR_b$ have no N—N or N—O bonds.

In some embodiments, A is C(O)NHOH.

In some embodiments, X is $(CR_d R_f)_j NR_b$ or $(CH_2)_j$.

In some embodiments, X is $(CR_d R_f)_j NR_b$.

In some embodiments, X is $CH_2 NR_b$, $CH_2 CH_2$, or $CH_2$.

In some embodiments, X is $CH_2 NR_b$.

In some embodiments, Y is $(CR_d R_f)_j NR_b$ or $(CH_2)_j$.

In some embodiments, Y is $(CH_2)_j$.

In some embodiments, Y is $CH_2 NR_b$, $CH_2 CH_2$, or $CH_2$.

In some embodiments, Y is $CH_2$.

In some embodiments, B is $(CH_2)_n$.

In some embodiments, B is $CH_2$.

In some embodiments, G is $(CH_2)_n$.

In some embodiments, G is $CH_2$.

In some embodiments, M is CO.

In some embodiments, U is absent or $NR_b$.

In some embodiments, U is absent.

In some embodiments, U' is absent, $C_{1-10}$ alkylene substituted with 0 to 5 $R_a$, O, C═O, or O—$(C_{1-10}$ alkylene).

In some embodiments, U' is absent or $C_{1-10}$ alkylene substituted with 0 to 5 $R_a$.

In some embodiments, U' is absent.

In some embodiments, V is $C_{3-13}$ carbocyclyl substituted with 0-5 $R_e$ or heterocyclyl substituted with 0-5 $R_e$.

In some embodiments, V is heterocyclyl substituted with 0-5 $R_e$.

In some embodiments, V is piperazin-1,4-diyl, piperidin-1,3-diyl, piperidin-1,4-diyl, 3,6-dihydropyridin-1,4(2H)-diyl, azetidin-1,4-yl, pyrrolidin-1,3-diyl, 2,5-dihydro-1H-pyrrol-1,3-diyl, 2,3,4,7-tetrahydro-1H-azepin-1,5-diyl, azepan-1,4-diyl, or 2,3-dihydro-1H-indol-1,5-diyl.

In some embodiments, V is piperazin-1,4-diyl.

In some embodiments, V' is $C_{1-8}$ alkyl, $C_{3-13}$ carbocyclyl substituted with 0-5 $R_e$ or heterocyclyl substituted with 0-5 $R_e$.

In some embodiments, V' is $C_{3-13}$ carbocyclyl substituted with 0-5 $R_e$ or heterocyclyl substituted with 0-5 $R_e$.

In some embodiments, V' is heterocyclyl substituted with 0-5 $R_e$.

In some embodiments, V' is pyridin-2-yl, pyridin-3-yl, pyridin-4-yl, 5-(trifluoromethyl)pyridin-2-yl, 3-(trifluoromethyl)pyridin-2-yl, 4,7,-dihydrothieno[2,3-c]pyridine-6(5H)-yl, 3,4-dihydroisoquinolin-2-(1H)-yl, 2,3-dihydro-1H-indol-1-yl, 4-phenyl-1,3-thiazol-2-yl, 4-tert-butyl-1,3-thiazol-2-yl, 2-thienyl, 3-thienyl, dibenzo[b,d]furan-4-yl, 1-methyl-1H-benzimidazol-6-yl, 1-ethyl-1H-benzimidazol-6-yl, 1,3-benzothiazol-6-yl, 1,4,5,6-tetrahydrobenzo[f]isoquinolin-3(2H)-yl, 2,3-dihydrobenzofuran-5-yl, 3,3-dimethyl-2,3-dihydrobenzofuran-5-yl, pyrazin-2-yl, 1,3,4,9-tetrahydro-2H-β-carbolin-2-yl, 9-methyl-1,3,4,9-tetrahydro-2H-β-carbolin-2-yl, 3,4,10,10a-tetrahydropyrazino[1,2-a]indol-2(1H)-yl, quinolin-2-yl, quinolin-4-yl, 2-methyl-quinolin-4-yl, 3,3a,8,8a-tetrahydroindeno[1,2-c]pyrrol-2(1H)-yl, piperidin-1-yl, 1,4,4a,5,6,10b-hexahydrobenzo[f]isoquinolin-3-(2H)-yl, 1,3,3a,4,5,9b-hexahydro-2H-benzo[e]isoindol-2-yl, 1,2,4,4a,5,6-hexahydro-3H-pyrazino[1,2-a]

quinolin-3-yl, 1-methyl-1H-indazol-5-yl, or 1,3-dihydro-1'H-spiro[indene-2,4'-piperdin]-1'-yl.

In some embodiments, V' is $C_{3-13}$ carbocyclyl substituted with 0-5 $R_e$.

In some embodiments, V' is phenyl, cyclohexyl, 2-naphthyl, or 5,6,7,8-tetrahydronaphthalen-2-yl.

In some embodiments, V' is phenyl substituted with 0-5 $R_e$.

In some embodiments, V' is phenyl.

In some embodiments, $R_b$ is H, T, $C_{1-6}$ alkylene-T, C(O)O$(CR_b'R_c')_r$-T, C(O)$(CR_b'R_c')_r$-T, or S(O)$_p(CR_b'R_c')_r$-T.

In some embodiments, $R_b$ is C(O)O$(CR_b'R_c')_r$-T.

In some embodiments, $R_b$ is C(O)OCH$_3$.

In some embodiments, $R_1$ is H.

In some embodiments, $R_2$ is H.

In some embodiments, the compound has Formula I wherein:

A is C(O)NHOH;

B and G are independently selected from $(CH_2)_n$, $(CH_2)_nC(O)$, $(CH_2)_nC(S)$, $(CR_dR_f)_nNR_8$, $(CR_dR_f)_nO(CR_dR_f)_r$, $(CR_dR_f)_nS(CR_dR_f)_r$, OC(O)NR$_8$, O, NR$_8$, S(O)$_m$, S, C(O)NR$_8(CR_dR_f)_n$ and C(O)$(CR_dR_f)_n$;

X and Y are independently selected from absent, $(CH_2)_j$, $C_{1-10}$ alkylene substituted with 0 to 3 $R_a$, NR$_b$, or $(CR_dR_f)_jNR_b$;

M is CO;

U is absent, $C_{1-10}$ alkylene substituted with 0 to 5 $R_a$, or NR$_b$;

V is absent, $C_{3-13}$ carbocyclyl substituted with 0-5 $R_e$ or heterocyclyl substituted with 0-5 $R_c$;

U' is absent, $C_{1-10}$ alkylene substituted with 0 to 5 $R_a$, O, NR$_b$S(O)$_m$, C=O, NR$_b$C(O), NR$_b$C(O)O, NR$_b$C(O)NR$_b$, C(O)O, O—(C$_1$-C$_{10}$ alkylene) or NR$_b$S(O)NR$_b$;

V' is H, $C_{1-8}$ alkyl, NR$_b$R$_c$, $C_{3-13}$ carbocyclyl substituted with 0-5 $R_e$ or heterocyclyl substituted with 0-5 $R_e$;

$R_e$ is H, T, $C_{1-8}$ alkylene-T, $(CR_b'R_c')_r$—O—$(CR_b'R_c')_r$-T, OH, Cl, F, Br, I, CN, NO$_2$, NR$^I$R$^{II}$, COR$^{III}$, OR$^{IV}$, CONR$^I$R$^{II}$, $C_{1-8}$ haloalkyl, $C_{3-13}$ carbocyclyl, or heterocyclyl;

$R_b$ and $R_c$ are independently selected from H, C(O)O$(CR_b'R_c')_r$-T and S(O)$_p(CR_b'R_c')_r$-T;

$R_d$ and $R_f$ are independently selected from H and $C_{1-6}$ alkyl;

$R_1$ and $R_2$ are independently selected from H and $C_{1-6}$ alkyl; and $R_4'$ and $R_5'$ are independently selected from H, C(O)NR$_a'$$(CR_c'R_b')_r$-T, C(O)O$(CR_b'R_c')_r$-T and S(O)$_p(CR_b'R_c')_r$-T.

In some embodiments, the compound has Formula I wherein:

A is C(O)NHOH;

B and G are independently selected from $(CH_2)_n$, $(CH_2)_nC(O)$, $(CR_dR_f)_nNR_8$, O, NR$_8$, S(O)$_m$, S, C(O)NR$_8(CR_dR_f)_n$ and C(O)$(CR_dR_f)_n$;

X and Y are independently selected from absent, $(CH_2)_j$, CH$_2$NR$_b$ or CH$_2$CH$_2$NR$_b$;

M is CO;

U is absent or NR$_b$;

V is heterocyclyl substituted with 0-5 $R_c$;

U' is absent, $C_{1-10}$ alkylene substituted with 0 to 5 $R_a$, or O;

V' is NR$_b$R$_c$, $C_{3-13}$ carbocyclyl substituted with 0-5 $R_e$ or heterocyclyl substituted with 0-5 $R_e$;

$R_e$ is H, T, OH, Cl, F, CN, or $C_{1-8}$ haloalkyl;

$R_b$ is H, C(O)NR$_a'$$(CR_c'R_b')_r$-T, C(O)O$(CR_b'R_c')_r$-T, C(O)$(CR_b'R_c')_r$-T, S(O)$_p(CR_b'R_c')_r$-T, $(CR_c'R_b')_r$—O—$(CR_c'R_b')_r$-T, C(NR$_a'$R$_a'$)(=N—CN) or C(NR$_a'$R$_a'$)(=CHNO$_2$);

$R_c$ is H, T, $C_{1-6}$ alkylene-T, $C_{2-8}$ alkenylene-T or $C_{2-6}$ alkynylene-T;

$R_d$ and $R_f$ are independently selected from H and $C_{1-6}$ alkyl;

$R_a'$ is H or $C_{1-6}$ alkyl;

$R_b'$ and $R_c'$ are independently selected from H, $C_{1-6}$ alkyl, OH, Cl, F, Br, I, CN, NO$_2$, NR$^I$R$^{II}$, OR$^{IV}$ and $C_{1-8}$ haloalkyl;

$R_1$ and $R_2$ are each H;

$R_4'$ and $R_5'$ are each H;

j is 1 or 2;

n is 0, 1, 2, 3 or 4; and r is 0, 1 or 2.

In some embodiments, the compound has Formula I wherein:

A is C(O)NHOH;

B and G are each $(CH_2)_n$;

X and Y are independently selected from absent, $(CH_2)_j$, CH$_2$NR$_b$ or NR$_b$CH$_2$CH$_2$;

M is CO;

U is absent;

V is heterocyclyl substituted with 0-5 $R_c$;

U' is absent, $C_{1-10}$ alkylene substituted with 0 to 5 $R_a$, or O;

V' is H, $C_{1-8}$ alkyl, NR$_b$R$_c$, $C_{3-13}$ carbocyclyl substituted with 0-5 $R_e$ or heterocyclyl substituted with 0-5 $R_e$;

$R_b$ is H, C(O)NR$_a'$$(CR_c'R_b')_r$-T, C(O)O$(CR_b'R_c')_r$-T, C(O)$(CR_b'R_c')_r$-T, C(NR$_a'$R$_a'$)(=N—CN) or C(NR$_a'$R$_a'$)(=CHNO$_2$);

$R_c$ is H, T, $C_{1-6}$ alkylene-T, $C_{2-8}$ alkenylene-T or $C_{2-6}$ alkynylene-T;

$R_a'$ is H or $C_{1-6}$ alkyl;

$R_b'$ and $R_c'$ are each, independently, H, $C_{1-6}$ alkyl, OH, Cl, F, Br, I, CN, NO$_2$, NR$^I$R$^{II}$, OR$^{IV}$ or $C_{1-8}$ haloalkyl;

$R_1$ and $R_2$ are each H;

$R_4'$ and $R_5'$ are each H;

j is 1 or 2;

n is 0, 1, 2, 3 or 4; and r is 0, 1 or 2.

In some embodiments, the compound has Formula I wherein:

A is C(O)NHOH;

B and G are each CH$_2$;

X is CH$_2$NR$_b$;

Y is CH$_2$;

M is CO;

U and U' are each absent;

V is piperazin-1,4-diyl;

V' is phenyl;

$R_b$ is C(O)O$(CR_b'R_c')_r$-T;

$R_b'$, $R_c'$, $R_1$, $R_2$, $R_4'$, $R_5'$ and T are each H; and r is 1.

In some embodiments, the compound of Formula I is methyl(6S,7S)-7-[(hydroxyamino)carbonyl]-6-[(4-phenylpiperazin-1-yl)carbonyl]-5-azaspiro[2.5]octane-5-carboxylate or pharmaceutically acceptable salt thereof.

In some embodiments, the compound is of the genera and/or species described in U.S. Pat. App. Pub. No. 2005/0250789 or 2005/0113344, each of which are incorporated herein in its entirety.

At various places in the present specification, substituents of the compounds of are disclosed in groups or in ranges. It is specifically intended that the invention include each and every individual subcombination of the members of such groups and ranges. For example, the term "$C_{1-6}$ alkyl" is specifically intended to individually disclose methyl, ethyl, C$_3$ alkyl, C$_4$ alkyl, C$_5$ alkyl, and C$_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

For compounds of the invention in which a variable appears more than once, each variable can be a different moiety selected from the Markush group defining the variable. For example, where a structure is described having two R groups that are simultaneously present on the same compound, the two R groups can represent different moieties selected from the Markush group defined for R.

At various places in the present specification, linking substituents are described. It is specifically intended that each linking substituent include both the forward and backward forms of the linking substituent. For example, $NR_b(CR_dR_f)_n$ includes both $NR_b(CR_dR_f)_n$ and $(CR_dR_f)_nNR_b$, $S(O)_mNR_b$ includes both $S(O)_mNR_b$ and $NR_bS(O)_m$, O—($C_1$-$C_{10}$ alkylene) includes both O—($C_1$-$C_{10}$ alkylene) and ($C_1$-$C_{10}$ alkylene)-O, and C(O)O includes both C(O)O and OC(O). Where the structure clearly requires a linking group, the Markush variables listed for that group are understood to be linking groups. For example, of the structure requires a linking group (e.g., U of Formula I) and the Markush group definition for that variable lists "alkyl," then it is understood that the "alkyl" represents a linking alkylene group.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. In some embodiments, an alkyl group can contain from 1 to about 20, from 2 to about 20, from 1 to about 10, from 1 to about 8, from 1 to about 6, from 1 to about 4, or from 1 to about 3 carbon atoms.

As used herein, the term "alkenyl" refers to an alkyl group having one or more double carbon-carbon bonds. Example alkenyl groups include ethenyl, propenyl, cyclohexenyl, and the like.

As used herein, the term "alkynyl" refers to an alkyl group having one or more triple carbon-carbon bonds. Example alkynyl groups include ethynyl, propynyl, and the like.

As used herein, the term "haloalkyl" refers to an alkyl group having one or more halogen substituents. As used herein, the term "haloalkyl" also refers to alkyl groups in which all of the hydrogen atoms are replaced with halogen atoms. Example haloalkyl groups include $CF_3$, $C_2F_5$, $CHF_2$, $CCl_3$, $CHCl_2$, $C_2Cl_5$, and the like. An alkyl group in which all of the hydrogen atoms are replaced with halogen atoms can also be referred to as "perhaloalkyl."

As used herein, the term "alkylene" or "alkylenyl" refers to a bivalent alkyl group. An example alkylene group is methylene or ethylene.

As used herein, the term "alkenylene" or "alkenylenyl" refers to a bivalent alkenyl group.

As used herein, the term "alkynylene" refers to a bivalent alkynyl group.

As used herein, "carbocyclyl" groups are saturated (i.e., containing no double or triple bonds) or unsaturated (i.e., containing one or more double or triple bonds) cyclic hydrocarbon moieties. Carbocyclyl groups can be mono- or polycyclic (e.g., having 2, 3 or 4 fused rings) or spirocyclic. Carbocyclyl groups can be aromatic (e.g., "aryl") or non-aromatic (e.g., "cycloalkyl"). Example carbocyclyl groups include cyclopropyl, cyclobutyl, cyclopentyl, cyclohexyl, cycloheptyl, cyclopentenyl, 1,3-cyclopentadienyl, cyclohexenyl, norbornyl, norpinyl, norcarnyl, adamantyl, phenyl, and the like. In some embodiments, carbocyclyl groups can have from about 3 to about 30 carbon atoms, about 3 to about 20, about 3 to about 10, or about 3 to about 7 carbon atoms.

As used herein, the term "aryl" refers to an aromatic carbocyclyl group including monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocyclyl groups including cyclized alkyl, alkenyl, and alkynyl groups. Cycloalkyl groups can include bi- or polycyclic (e.g., having 2, 3 or 4 fused rings) ring systems as well as spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of pentane, pentene, hexane, and the like.

As used herein, "heterocyclyl" or "heterocycle" refers to a saturated or unsaturated cyclic group wherein one or more of the ring-forming atoms of the is a heteroatom such as oxygen, sulfur, or nitrogen. Heterocyclyl groups can be aromatic (e.g., "heteroaryl") or non-aromatic (e.g., "heterocycloalkyl"). Heterocyclyl groups can also correspond to hydrogenated and partially hydrogenated heteroaryl groups. Heterocyclyl groups can include mono- or polycyclic (e.g., having 2, 3 or 4 fused rings) ring systems. Heterocyclyl groups can be characterized as having 3-20 ring-forming atoms. In some embodiments, heterocyclyl groups can contain, in addition to at least one heteroatom, from about 1 to about 20, about 2 to about 10, or about 2 to about 7 carbon atoms and can be attached through a carbon atom or heteroatom. In further embodiments, the carbon atoms or hetereoatoms in the heterocyclyl or heterocycle ring can be oxidized (to form, e.g., a carbonyl, sulfinyl, sulfonyl, or other oxidized nitrogen or sulfur linkage) or a nitrogen atom can be quaternized. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like, as well as any of the groups listed below for "heteroaryl" and "heterocycloalkyl." Further example heterocycles include pyrimidinyl, phenanthridinyl, phenanthrolinyl, phenazinyl, phenothiazinyl, phenoxathiinyl, phenoxazinyl, phthalazinyl, piperazinyl, piperidinyl, 3,6-dihydropyridyl, 1,2,3,6-tetrahydropyridyl, 1,2,5,6-tetrahydropyridyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrazolyl, 6H-1,2,5-thia-diazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, quinazolinyl, quinolinyl, 4H-quinolizinyl, quinoxalinyl, quinuclidinyl, acridinyl, azocinyl, benzimidazolyl, benzofuranyl, benzothiofuranyl, benzo-thiophenyl, benzoxazolyl, benzthiazolyl, benztriazolyl, benztetrazolyl, benzisoxazolyl, benzisothiazolyl, benzimidazolinyl, methylenedioxyphenyl, morpholinyl, naphthyridinyl, decahydroquinolinyl, 2H,6H-1,5,2dithiazinyl, dihydrofuro[2,3-b]tetrahydrofuran, furanyl, furazanyl, carbazolyl, 4aH-carbazolyl, carbolinyl, chromanyl, chromenyl, cinnolinyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl and isoxazolyl. Further examples of heterocyclyl groups and heterocycles include pyridin-2-yl, pyridin-3-yl, pyridin-4-yl, 5-(trifluoromethyl)pyridin-2-yl, 3-(trifluoromethyl)pyridin-2-yl, 4,7,-dihydrothieno[2,3-c]pyridine-6(5H)-yl, 3,4-dihydroisoquinolin-2-(1H)-yl, 2,3-dihydro-1H-indol-1-yl, 4-phenyl-1,3-thiazol-2-yl, 4-tert-butyl-1,3-thiazol-2-yl, 2-thienyl, 3-thienyl, dibenzo[b,d]furan-4-yl, 1-methyl-1H-benzimidazol-6-yl, 1-ethyl-1H-benzimidazol-6-yl, 1,3-benzothiazol-6-yl, 1,4,5,6-tetrahydrobenzo[f]isoquinolin-3(2H)-yl, 2,3-dihydrobenzofuran-5-yl, 3,3-dimethyl-2,3-dihydrobenzofuran-5-yl pyrazin-2-yl, 1,3,4,9-tetrahydro-2H-β-carbolin-2-yl, 9-methyl-1,3,4,9-tetrahydro-2H-β-carbolin-2-yl, 3,4,10,10a-tetrahydropyrazino[1,2-a]-indol-2(1H)-yl, quinolin-2-yl, quinolin-4-yl, 2-methyl-quinolin-4-yl, 3,3a,8,8a-tetrahydroindeno[1,2-c]pyrrol-2(1H)-yl, piperidin-1-yl, 1,4,4a,5,6,10b-hexahydrobenzo[f]isoquinolin-3-(2H)-yl, 1,3,3a,4,5,9b-hexahydro-2H-benzo[e]isoindol-2-yl, 1,2,4,4a,5,6-hexahydro-3H-pyrazino[1,2-a]quinolin-3-yl, 1-methyl-1H-indazol-5-yl, and 1,3-dihydro-1'H-spiro[indene-2,4'-piperdin]-1'-yl groups. Further example heterocyclyl groups and heterocycles include piperazin-1,4-diyl, piperidin-1,3-diyl, piperidin-1,4-diyl, 3,6-dihydropyridin-1,4(2H)-diyl, azetidin-1,4-yl, pyrrolidin-1,3-diyl, 2,5-dihydro-1H-pyrrol-1,3-diyl, 2,3,4,7-tetrahydro-1H-azepin-1,5-diyl, azepan-1,4-diyl, and 2,3-dihydro-1H-indol-1,5-diyl groups. Heterocyclyl groups and heterocycles also include fused ring and spiro compounds containing, for example, the above heterocycles.

As used herein, the term "heteroaryl" groups are aromatic heterocyclyl groups and include monocyclic and polycyclic (e.g., having 2, 3 or 4 fused rings) aromatic hydrocarbons that have at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, the term "heterocycloalkyl" refers to non-aromatic heterocyclyl groups including cyclized alkyl, alkenyl, and alkynyl groups that have at least one heteroatom ring member such as nitrogen, oxygen, or sulfur. In some embodiments, the carbon atoms or heteroatoms in the heterocycloalkyl group can be oxidized (to form, e.g., a carbonyl, sulfinyl, sulfonyl, etc.) or a nitrogen atom can be quaternized. Example heterocycloalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, the terms "halo" or "halogen" refer to a fluorine, chlorine, bromine, or iodine atom.

As used herein, the term "alkoxy" refers to an -O-alkyl group. Example alkoxy groups include methoxy, ethoxy, n-propoxy, isopropoxy, n-butoxy, tert-butoxy, and the like.

As used herein, the term "aryloxy" refers to an -O-aryl group. An example aryloxy group is phenoxy.

As used here, the term "haloalkoxy" refers to an -O-haloalkyl group. An example haloalkoxy group is $OCF_3$. As used herein, the term "carbocyclyloxy" refers to an -O-carbocyclyl group. Example carbocyclyloxy groups are cyclohexoxy and phenoxy.

As used herein, the term "heterocyclyloxy" refers to an -O-heterocyclyl group. An example heterocycyl groups is pyridin-4-yl-oxy.

As used herein, the term "carbocyclylalkyl" refers to an alkyl moiety substituted by a carbocyclyl group. Example carbocyclylalkyl groups include "aralkyl" (alkyl substituted by aryl ("arylalkyl")) and "cycloalkylalkyl" (alkyl substituted by cycloalkyl). In some embodiments, carbocyclylalkyl groups have from 4 to 24 carbon atoms.

As used herein, the term "heterocyclylalkyl" refers to an alkyl moiety substituted by a heterocyclyl group. Example heterocyclylalkyl groups include "heteroarylalkyl" (alkyl substituted by heteroaryl) and "heterocycloalkylalkyl" (alkyl substituted by heterocycloalkyl). In some embodiments, heterocyclylalkyl groups have from 3 to 24 carbon atoms in addition to at least one heteroatom ring member, such as oxygen, nitrogen, or sulfur As used herein, the term "amino" refers to an $NH_2$ group. The term "alkylamino" refers to an amino group substituted by an alkyl group, and the term "dialkylamino" refers to an amino group substituted by two alkyl groups.

As used herein, the term "aminocarbonyl" refers to $CONH_2$.

As used herein, the term "alkylaminocarbonyl" refers to CONH(alkyl).

As used herein, the term "dialkylaminocarbonyl" refers to $CON(alkyl)_2$.

As used herein, the term "carboxy" or "carboxyl" refers to COOH.

As used herein, the term "carboxy alkyl ester" refers to COO-alkyl.

As used herein, the term "carboxy aryl ester" refers to COO-aryl.

As used herein, the term "cyano" refers to CN, where the carbon and nitrogen atoms are triply bonded to each other.

As used herein, the term "hydroxy" refers to OH

As used herein, the term "mercapto" refers to SH.

As used herein, the term "nitro" refers to $NO_2$.

As used herein, the term "sulfinyl" refers to SO.

As used herein, the term "sulfonyl" refers to $SO_2$.

As used herein, the term "aminosulfonyl" refers to $SO_2NH_2$.

As used herein, the term "alkylaminosulfonyl" refers to $SO_2NH(alkyl)$.

As used herein, the term "dialkylaminosulfonyl" refers to $SO_2N(alkyl)_2$.

As used herein, the term "arylsulfonyl" refers to $SO_2$-aryl.

As used herein, the term "arylsulfinyl" refers to SO-aryl.

As used herein, the term "alkylsulfonyl" refers to $SO_2$-alkyl.

As used herein, the term "alkylsulfinyl" refers to SO-alkyl.

Unless otherwise indicated, the compounds of Formula I are meant to include pharmaceutically acceptable salts, prodrugs, enantiomers, diastereomers, racemic mixtures, crystalline forms, non-crystalline forms, amorphous forms, hydrates and solvates thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable risk/benefit ratio.

The present invention also includes pharmaceutically acceptable salts of the compounds of Formula I. As used herein, "pharmaceutically acceptable salts" refers to derivatives of the disclosed compounds wherein the parent compound is modified by converting an existing acid or base moiety to its salt form. Certain specific compounds of Formula I may contain both basic and acidic functionalities that allow the compounds to be converted into either base or acid addition salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of a parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The compounds of Formula I can possess chiral or asymmetric carbon atoms (e.g., having one or more stereocenters); the racemates, diastereomers, enantiomers, and individual optical isomers are all intended to be encompassed within the scope of the present invention, unless otherwise indicated. Compounds of Formula I that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. The compounds of Formula I can also include cis and trans geometric isomers which may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of Formula I also include tautomeric forms, such as keto-enol tautomers. Tautomeric forms can be in equilibrium or sterically locked into one form by appropriate substitution.

Some of the compounds of Formula I can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention. Compounds of Formula I further include anyhydrous and non-solvated forms.

Compounds of Formula I can also include all isotopes of atoms occurring in the intermediates or final compounds. Isotopes include those atoms having the same atomic number but different mass numbers. For example, isotopes of hydrogen include tritium and deuterium.

In addition to salt forms, the present invention also includes prodrugs of the compounds of Formula I. As used herein, the term "prodrugs" refer to any covalently bonded carriers which release the active parent drug when administered to a patient. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a patient, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entireties. Additionally, prodrugs can be converted to the compounds of the present invention by chemical or biochemical methods in an ex-vivo environment. For example, prodrugs can be slowly converted to the compounds of Formula I when placed in a transdermal patch reservoir with a suitable enzyme or chemical reagent.

The compounds of Formula I can be synthesized as described for the compounds of U.S. Patent Appl. No. 2004/0259896, which is incorporated herein by reference in its entirety. The compounds of Formula I of the present invention can also be prepared by a variety of methods known to one skilled in the art of organic synthesis, as well as by variations on such methods as appreciated by those skilled in the art.

Antibodies

The term "antibody" as referred to herein includes whole antibodies and any antigen binding fragment (i.e., "antigen-binding portion") or single chain thereof Generally, "antibody" refers to a glycoprotein comprising at least two heavy (H) chains and two light (L) chains inter-connected by disulfide bonds, or an antigen binding portion thereof Each heavy chain is comprised of a heavy chain variable region ($V_H$) and a heavy chain constant region. The heavy chain constant region is comprised of three domains, $C_{H1}$, $C_{H2}$ and $C_{H3}$. Each light chain is comprised of a light chain variable region ($V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding portion" of an antibody (or "antibody portion"), as used herein, refers to one or more fragments of an antibody that has the ability to specifically bind to an antigen (e.g., CD30). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment composed of the VH and CHI domains; (iv) a Fv fragment consisting of the $V_L$ and $V_H$ domains of a single arm of an antibody, (v) a dAb fragment (Ward et al., (1989) Nature 341:544-546), which is composed of a $V_H$ domain; and (vi) an isolated complementarity determining region (CDR). Furthermore, although the two domains of the Fv fragment, $V_L$ and $V_H$ are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883. Such single chain antibodies are also intended to be encompassed within the term "antigen-binding portion" of an antibody. These antibody fragments are obtained using conventional techniques known to those with skill in the art, and the fragments can be screened for utility in the same manner as for full or intact antibodies.

The term "immunotherapeutic" is meant to refer to an antibody or antibody-conjugate useful in the treatment of diseases. Example immunotherapeutics of the invention include anti-CD30 antibodies and anti-CD30 antibody-conjugates.

Antibodies against CD30 are well known in the art. In some embodiments, an antibody used according to the methods of the present invention is chimeric, humanized or human. In further embodiments, the antibody is a monoclonal antibody. In yet further embodiments, the antibody is a fully human antibody. Suitable antibodies include those that bind specifically to human CD30 with high affinity, such as those exhibiting a binding affinity to CD30 with an affinity constant of at least about $10^7$ M$^{-1}$, at least about $10^8$ M$^{-1}$, at least about $10^9$ M$^{-1}$, at least about $10^{10}$ M$^{-1}$, or stronger. Suitable antibodies further include those that exhibit an association constant ($K_{assoc}$) with CD30 of at least about $10^3$, at least about $10^4$, or at least about $10^5$ M$^{-1}$ s$^{-1}$. In some embodiments, the dissociation constant ($K_{dis}$) from CD30 has a value of about $10^{-3}$ s$^{-1}$ or less, about $10^{-4}$ s$^{-1}$ or less, or about $10^{-5}$ s$^{-1}$ or less, or about $10^{-6}$ s$^{-1}$ or less. In some embodiments, suitable antibodies have the ability to opsonize a cell expressing CD30, to inhibit growth and/or mediate phagocytosis and killing of cells expressing CD30 (e.g., a tumor cell) in the presence of human effector cells at a concentration of about 10 µg/mL or less (e.g., in vitro), and/or to bind to CD30 and inhibit CD30 function (e.g., CD30 mediated effects) by partially or completely blocking a CD30 ligand binding to CD30 (examples of CD30 ligands include, e.g., CD 153, TRAF1, TRAF2, TRAF3 and TRAF5).

In some embodiments, the antibody binds to human CD30 with a $K_D$ of about $5 \times 10^{-9}$ M or less, a $K_D$ of $4 \times 10^{-9}$ M or less, a $K_D$ of $3.5 \times 10^{-9}$ M or less, a $K_D$ of $3 \times 10^{-9}$ M or less or a $K_D$ of $2.8 \times 10^{-9}$ M or less.

Standard assays to evaluate the binding ability of antibodies toward CD30 are known in the art, including for example, ELISAs, Western blots and RIAs. The binding kinetics (e.g., binding affinity) of the antibodies also can be assessed by standard assays known in the art, such as by Biacore analysis.

Example antibodies suitable for use in the methods of the invention include Example anti-CD30 antibodies include, e.g., 5F1 1, HeFi-1, ClO, M44, AClO, Ber-H2, HRS-1, HRS-3, HRS-4, Ki-1, Ki-2, Ki-3, Ki-4, Ki-5, Ki-6, Ki-7, IRac, M67, as well as the human monoclonal antibodies 17G1, 2H9 and 5F11, including antigen-binding fragments of any of the aforementioned, which are characterized and described in U.S. Pat. App. Pub. No. 2004/0006215 (incorporated herein by reference in its entirety). Further suitable antibodies, including human, humanized, chimeric, modified, and engineered antibodies as well as their methods of preparation and use as therapeutics, are described in WO 2006/039644 which is incorporated herein by reference in its entirety.

The antibodies of the present invention can further be monospecific, bispecific, trispecific or of greater multispecificity. Multispecific antibodies may be specific for different epitopes of CD30 or may be specific for both CD30 as well as for a heterologous protein. See, e.g., PCT publications WO 93/17715; WO 92/08802; WO 91/00360; WO 92/05793; Tutt, et al., 1991, J. Immunol. 147:60-69; U.S. Pat. Nos. 4,474,893; 4,714,681; 4,925,648; 5,573,920; 5,601,819; Kostelny et al., 1992, J. Immunol. 148:1547-1553.

Antibodies can further include derivatives that are modified, e.g., by the covalent attachment of any type of molecule to the antibody such that covalent attachment does not prevent the antibody from binding to CD30. For example, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In certain embodiments, the antibodies are human antigen-binding antibody fragments and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, can comprise the variable region(s) alone or in combination with the entirety or a portion of the following: hinge region, $C_{H1}$, $C_{H2}$, $C_{H3}$ and $C_L$ domains. Also included in the invention are antigen-binding fragments also comprising any combination of variable region(s) with a hinge region, $C_{H1}$, $C_{H2}$, $C_{H3}$ and $C_L$ domains. Preferably, the antibodies are human, murine (e.g., mouse and rat), donkey, sheep, rabbit, goat, guinea pig, camelid, horse, or chicken.

As used herein, "human" antibodies include antibodies having the amino acid sequence of a human immunoglobulin and include antibodies isolated from human immunoglobulin libraries, from human B cells, or from animals transgenic for one or more human immunoglobulin, as described for example in U.S. Pat. No. 5,939,598.

Antibody-Conjugates

According to further aspects of the invention, antibodies can be conjugated to a therapeutic moiety, such as a cytotoxin, a radiotoxin, a drug, or other moiety and are referred to herein as antibody-conjugates or conjugates. Preferably, the conjugate moiety does not substantially interfere with the ability of the antibody to bind with CD30.

Techniques for conjugating therapeutic moieties to antibodies are well known, see, e.g., Arnon et al, "Monoclonal Antibodies For Immunotargeting Of Drugs hi Cancer Therapy", in Monoclonal Antibodies And Cancer Therapy, Reisfeld et al (eds.), pp. 243-56 (Alan R. Liss, Inc. 1985); Hellstrom et al, "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents hi Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody hi Cancer Therapy", in Monoclonal Antibodies For Cancer Detection And Therapy, Baldwin et al. (eds.), pp. 303-16 (Academic Press 1985), and Thorpe et al, "The Preparation And Cytotoxic Properties Of Antibody-Toxin Conjugates", Immunol. Rev., 62:119-58 (1982).

Conjugate moieties can be attached to antibodies via linker technology available in the art. Examples of linker types include, for example, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C J. (2001) [Lambda]Jv. DrugDeliv. Rev. 53:247-264.

In some embodiments, the antibody is conjugated with a cytotoxin. A cytotoxin includes any agent that kills cells or inhibits cell growth. Example cytotoxins include chemotherapeutics such as any in the following classes of chemotherapeutic agents: alkylating agents, anthracyclines, antibiotics, antifolates, antimetabolites, antitubulin agents, auristatins, chemotherapy sensitizers, DNA minor groove binders, DNA replication inhibitors, duocarmycins, etoposides, fluorinated pyrimidines, lexitropsins, nitrosoureas, platinols, purine antimetabolites, puromycins, radiation sensitizers, steroids, taxanes, topoisomerase inhibitors, and vinca alkaloids. Examples of individual chemotherapeutics that can be conjugated to an antibody include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

Further cytotoxins which can be conjugated to antibodies include enzymatically active toxins, or active fragments thereof, such as abrin, ricin A, pseudomonas exotoxin, diphtheria toxin, and the like.

Further example cytotoxins include doxorubicin, paclitaxel, melphalan, vinca alkaloids, methotrexate, mitomycin C, etoposide, and others. In addition, potent agents such CC-1065 analogs, calichiamicin, maytansine, analogs of dolastatin 10, rhizoxin, and palytoxin can be linked to the anti-CD30 antibodies using conditionally stable linkers to form potent immunoconjugates.

Further example cytotoxins include DNA minor groove binders, including enediynes and lexitropsins, duocarmycins, taxanes (including paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epithilone A and B, estramustine, cryptophysins, cemadotin, maytansinoids, dolastatins, e.g., auristatin E, dolastatin 10, MMAE, discodermolide, eleutherobin, and mitoxantrone.

In some embodiments, the cytotoxin is calicheamicin, an auristatin such as auristatin E or a derivative thereof. The synthesis and structure of auristatin E, also known in the art as dolastatin-10, and its derivatives are described in U.S. patent application Ser. Nos. 09/845,786 and 10/001,191; in the International Patent Application No.: PCT/US02/13435, in U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, all of which are incorporated herein by reference in their entireties.

In some embodiments, the cytotoxin is a DNA minor groove binding agent.

In certain embodiments, the drug an anti-tubulin agent. Examples of anti-tubulin agents include, but are not limited to, taxanes (e.g., Taxol® (paclitaxel), docetaxel), T67 (Tularik), vincas, and auristatins (e.g., auristatin E, AEB, AEVB, MMAE, AEFP). Antitubulin agents included in this class are also: vinca alkaloids, including vincristine and vinblastine, vindesine and vinorelbine; taxanes such as paclitaxel and docetaxel and baccatin derivatives, epithilone A and B, nocodazole, colchicine and colcimid, estramustine, cryptophysins, cemadotin, maytansinoids, combretastatins, dolastatins, discodermolide and eleutherobin. In some embodiments, the cytotoxin is a maytansinoid, a group of anti-tubulin agents. In a more specific embodiment, the drug is maytansine. Further, in a specific embodiment, the cytotoxic agent is DM-1 (ImmunoGen, Inc.; see also Chari et al., 1992, Cancer Res 52:127-131). In another specific embodiment, the drug is an AEFP. In certain embodiments, the cytoxin is a dolastatin such as an auristatin. In a specific embodiment of the invention, the cytotoxin is MMAE (auristatin E). In another specific embodiment of the invention, the cytotoxin is AEFP.

Antibodies can also be conjugated with a radiotoxins. A radiotoxin is meant to refer to any moiety containing a radioactive isotope. Examples of radioactive isotopes that can be conjugated to antibodies for use diagnostically or therapeutically include, but are not limited to, $^{211}$At, $^{67}$Cu, $^{131}$I, $^{125}$I, $^{90}$Y, $^{186}$Re, $^{188}$Rc, $^{153}$Sm, $^{212}$Bi, $^{32}$P, and $^{212}$Pb as well as radioactive isotopes of Lu. Methods for preparing radioimmunconjugates are routine in the art. Examples of antibodies conjugated with radiotoxin are commercially available, including Zevalin™ (IDEC Pharmaceuticals) and Bexxar™ (Corixa Pharmaceuticals).

Other drugs and therapeutic agents that can be conjugated with antibodies include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (11) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Also contemplated are drugs such as methotrexate (Endo et al., 1987, Cancer Research 47:1076-1080), daunomycin (Gallego et al., 1984, Int. J. Cancer. 33:737-744), mitomycin C (MMC) (Ohkawa et al., 1986, Cancer Immunol. Immunother. 23:81-86) and vinca alkaloids (Rowland et al., 1986, Cancer Immunol Immunother. 21:183-187) have been attached to antibodies and the derived conjugates have been investigated for anti-tumor activities.

Suitable anti-CD30 antibodies, their conjugates, and preparations thereof are described in U.S. Pat. App. Pub. No. 2004/0018194, which is incorporated herein by reference in its entirety.

Treatable Diseases and Conditions

The combination therapy described herein is useful in the treatment of a variety of diseases which are characterized by the presence (e.g., the expression) of CD30. An example disease treatable by the combinations disclosed herein is a CD30 positive cancer such as a CD30 positive lymphoma. Detection of CD30 in diseased tissues can be carried out by routine methods. In some embodiments, the disease is further characterized by the shedding of CD30, typically resulting in the presence of circulating sCD30 which can be routinely detected by methods known in the art.

Example diseases which are often characterized by expression of CD30 and treatable by the methods described herein include, Hodgkin's disease (HD), Burkitt's lymphoma, anaplastic large-cell lymphoma (ALCL), cutaneous T-cell lymphoma, nodular small cleaved-cell lymphoma, lymphocytic lymphoma, peripheral T-cell lymphomas, Lennert's lymphoma, immunoblastic lymphoma, T-cell leukemia, adult T-cell leukemia (ATL), entroblastic/centrocytic follicular lymphoma, and the like. In some embodiments, the disease is Hodgkin's disease (HD), anaplastic large-cell lymphoma (ALCL), or adult T-cell leukemia (ATL).

Further example diseases include rheumatoid arthritis (RA), systemic lupus erythematosus, systemic sclerosis, atopic dermatitis, Grave's disease, Hashimoto's thyroiditis, Wegner's granulaomtosis, Omen's syndrome, chronic renal failure, acute infectious mononucleosis, HIV, herpes virus associated diseases, and the like.

The combination therapy described herein is further useful in reducing toxicity in a patient of an administered anti-CD30 antibody-conjugate where, for example, the conjugate is a cytotoxin or radiotoxin. In some embodiments, the toxicity is organ toxicity such as liver, spleen, or bone marrow toxicity. In some embodiments, the toxicity is vascular leak syndrome.

The combination therapy described herein is further useful in increasing the maximum tolerated dosage in a patient of an administered anti-CD30 antibody-conjugate where, for example, the conjugate is a cytotoxin or radiotoxin.

Administration

According to the present invention, patients are treated with a combination of at least one CD30 sheddase inhibitor, such as a compound of Formula I, and at least one antibody or antibody conjugate that binds to CD30. The administration of each of these substances can be carried out simultaneously or sequentially. For simultaneous administration, a mixture or composition containing both components can be given to the patient. For sequential administration, each component can be given to the patient separately, at different points in time. However, it is desirable that the physiological effects of both the compound and antibody (or conjugate thereof) overlap. Regardless of how the components are administered, it is desirable that the administered compound of Formula I acts as a sheddase inhibitor for at least some time during which the antibody (or conjugate thereof) binds to CD30 in the patient such that the benefits of the combination are realized.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Pharmaceutical Formulations and Dosage Forms

When employed as pharmaceuticals, the combinations of compounds, antibodies, and/or antibody-conjugates of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain combinations of compounds, antibodies, and antibody-conjugates together with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredients. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The combined active ingredients can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

Various delivery systems are known and can be used to administer protein therapeutics such as antibodies or antibody-conjugates. These systems include encapsulation in liposomes, microparticles, microcapsules, and the like. Methods of introduction include but are not limited to intradermal, intramuscular, intraperitoneal, intravenous, subcutaneous, intranasal, epidural, and oral routes. Proteins can be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In some embodiments, administration is carried out by injection by means of a catheter, suppository, or an implant, where the implant is composed of a porous, non-porous, or gelatinous material, including a membrane, such as a sialastic membrane, or a fiber. When administering a protein, including an antibody care must typically be taken to use materials to which the protein does not absorb.

In some embodiments, pharmaceutical agents and combinations thereof can be delivered in a vesicle such as a liposome (see Langer, 1990, Science 249:1527-1533; Treat et al., 1989, in Liposomes in the Therapy of Infectious Disease and Cancer, Lopez-Berestein and Fidler (eds.), Liss, N.Y., pp. 353-365).

In some embodiments, pharmaceutical agents and combinations thereof can be delivered in a controlled release system. For example, a pump can be used (see Langer, supra; Sefton, 1989, CRC Crit. Ref. Biomed. Eng. 14:201; Buchwald et al., 1980, Surgery 88:507; Saudek et al., 1989, N. Engl. J. Med. 321:574) or polymeric materials can be used (see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, N.Y.; Ranger and Peppas, 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105).

In some embodiments, the pharmaceutical agents and combinations thereof are formulated in accordance with routine procedures as a pharmaceutical composition adapted for intravenous administration to human beings. Typically, compositions for intravenous administration are solutions in sterile isotonic aqueous buffer. Where necessary, the pharmaceutical of the invention may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceuticals of the invention are to be administered by infusion, it can be dispensed with an infusion bottle containing sterile pharmaceutical grade water or saline. Where the pharmaceuticals of the invention is administered by injection, an ampoule of sterile water for injection or saline can be provided so that the ingredients may be mixed prior to administration.

Further Combinations

The combination of sheddase inhibitor and antibody (or antibody-conjugate) can be administered in combination with irradiation and/or one or more additional therapeutic agents.

In certain embodiments, the additional therapeutic agent is an immunosuppressive agent such as gancyclovir, acyclovir, etanercept, rapamycin, cyclosporine or tacrolimus. In other embodiments, the immunosuppressive agent is an antimetabolite, a purine antagonist (e.g., azathioprine or mycophenolate mofetil), a dihydrofolate reductase inhibitor (e.g., methotrexate), a glucocorticoid. (e.g., cortisol or aldosterone), or a glucocorticoid analogue (e.g., prednisone or dexamethasone). In yet other embodiments, the immunosuppressive agent is an alkylating agent (e.g., cyclophosphamide). In yet other embodiments, the immunosuppressive agent is an anti-inflammatory agent, including but not limited to a cyclooxygenase inhibitor, a 5-lipoxygenase inhibitor, and a leukotriene receptor antagonist.

In the case of irradiation treatment, the irradiation can be gamma rays or X-rays. For a general overview of radiation therapy, see Hellman, Chapter 12: Principles of Radiation Therapy Cancer, in: Principles and Practice of Oncology, DeVita et al., eds., 2nd. Ed., J. B. Lippencott Company, Philadelphia.

In further embodiments, the additional therapeutic agent is a chemotherapeutic agent such as any of those recited herein.

In embodiments where the antibody is conjugated to a pro-drug converting enzyme, is a pro-drug can be an additional therapeutic agent. Administration of the pro-drug can be concurrent with administration of the antibody-conjugate, or follow administration by at least an hour to up to one week, for example about five hours, 12 hours, or a day. Example prodrugs include a benzoic acid mustard, an aniline mustard, a phenol mustard, p-hydroxyaniline mustard-glucuronide, epirubicin-glucuronide, adriamycin-N phenoxyaceryl, N-(4'-hydroxyphenyl acetyl)-palytoxin doxorubicin, melphalan, nitrogen mustard-cephalosporin, .beta.-phenylenediamine, vinblastine derivative-cephalosporin, cephalosporin mustard, cyanophenylmethyl-.beta.-D-gluco-pyranosiduronic acid, 5-(adaridin-1-yl-)2,4-dinitrobenzamide, or methotrexate-alanine.

In further embodiments, the additional therapeutic agent is a proteasome inhibitor. Suitable proteasome inhibitors are described, for example, in U.S. Pat. Nos. 5,780,454; 6,066,730; 6,083,903; 6,297,217; 6,465,433; 6,548,668; 6,617,317; and 6,747,150, each of which is incorporated by reference herein in its entirety.

EXAMPLES

The impact of ADAM inhibition using one of the compounds described in this application on enhancing the positive therapeutic effects of anti-CD30 directed therapies can be illustrated in various ways by one skilled in the art, including the experiments described below.

Example A

Cell Culture

CD30 is overexpressed on the surface of, e.g., Hodgkin's lymphoma and anaplastic large cell lymphoma as well as on cell lines such as, e.g., the Karpas 299 lymphoma. One can evaluate the influence of a compound, such as described in this application, on the efficacy of anti-CD30 protein based therapies using such cells or cell lines. In cell culture, the addition of compound at a set concentration can be studied in combination with varying amounts of anti-CD30 targeted therapy and evaluated over the time period of 1 hour to 5 days, depending on the assay used, for the antitumor effect against these malignant cells or cell lines expressing CD30. Such an evaluation might include a negative effect on cell growth as determined using reagents that measure cell proliferation, a negative effect on the activity of a growth factor signaling pathway using measures such as phosphorylated ERK, or an enhancing effect on cell death by apoptosis using markers such as decreased phosphorylated Akt protein or increased activation of caspase enzymes. Example protocols are provided below.

Effects on cell signaling. Karpas cells ($2\times10^5$/well) are seeded into 12-well plates. After overnight culture, the medium is replaced with fresh media containing anti-CD30 antibody (0.1-10 µg/ml) and/or sheddase compound at various concentrations (10 nM-10 µM). Cells are re-fed once on day 3. After 5 days, the cells are lysed in 200 µls of ice-cold RIPA buffer (10 mM Tris, pH 7.2, 150 mM NaCl, 1% Triton X-100, 1% deoxycholic acid, 0.1% SDS, 50 µg/ml leupeptin, 50 µg/ml aprotinin, 1 mM sodium vanadate, 50 mM sodium fluoride, 1 mM phenylmethylsulfonyl fluoride), and the supernatants/cell extracts are collected by centrifugation. Normally, 15 µls of extract is diluted with 2× Laemmli sample buffer (Bio-Rad, Hercules, Calif.), and boiled for 5 min before loading onto Tris-Glycine gels (Invitrogen). Following electrophoresis, the proteins are transferred onto PVDF membrane (PerkinElmer, Boston, Mass.). The membrane is blocked in PBS containing 5% milk and 0.1% Tween-20 for 1 hr and then incubated with primary antibody (anti-pERK1/2 or anti-phospho-AKT) in blocking solution for 1 hr at room temperature. After 3 washes in PBS containing 0.1% Tween-20, the membrane is incubated with horseradish peroxidase-conjugated goat anti-rabbit IgG diluted in blocking solution for 1 hr at room temperature. After final 3 washes, the blot is incubated with chemiluminescence detection reagent for 5 min and exposed to X-ray film.

Cell proliferation assay. Both cell counting and BrdU incorporation assay can be performed. For cell counting, Karpas cells ($1\times10^5$/well) are seeded into 12-well plates, and after overnight culture, cells are treated for a specific time period with or without test compound, and/or anti-CD30 antibodies at concentrations as in the cell signaling studies. For 6-day treatment, the media is replaced after the first 3 days with fresh media containing the same concentrations of the compound and/or anti-CD30 antibody. At the end of each experiment, viable cells are counted with a hemacytometer after trypan blue staining. For BrdU incorporation, the assay is performed by using a calorimetric Cell Proliferation ELISA kit per manufacturer's instructions (Roche Molecular Biochemicals, Indianapolis, Ind.). Briefly, Karpas cells ($5\text{-}10\times10^3$/well) are seeded in 96 well plates and cultured overnight. The next day, the media is replaced with fresh media containing sheddase compound, and/or anti-CD30 antibody at concentrations as in the cell signaling studies. After 3 or 6-days of incubation, BrdU labeling solution is added into the medium at 10 µM final concentration, and cells are incubated for an additional 4-5 hrs at 37° C. The rest of the procedure is performed according to the manufacturer's instructions. Finally, the results are obtained by using a microplate reader (Molecular Devices), monitoring color development. Multiple readings at various time points are obtained, and results in the linear range of the assay are used. The data are presented as average values and standard deviations.

Apoptosis assay. Karpas cells ($1\times10^4$/well) are seeded in 96 well plates and cultured overnight. The next day, the media is replaced with fresh media containing anti-CD30 antibody and/or sheddase compound at concentrations as in the cell signaling studies. After 3 days of treatment, cell death is measured with the Cell Death Detection ELISAPLUS kit (Roche Molecular Biochemicals) according to the manufacturer's instructions. The final results are obtained with a microplate reader monitoring color development. Multiple readings at various time points are obtained, and results in the linear range of the assay are used. Average numbers and standard deviations are calculated and presented.

Example B

In Rodent Xenograft Models

Severe combined immunodeficiency (SCID) mice hosting human CD30-positive lymphoma cells as xenografts can be treated with the anti-CD30 targeted protein based therapies in the presence or absence of one of the compounds described in this application. Dosing of animals hosting such tumors with compound can be by oral route, by subcutaneous or intraperitoneal injection or by continuous infusion using osmotic pumps or compound impregnated pellets. Concomitantly treating with an anti-CD30 directed protein based therapy should demonstrate additive, superadditive or synergistic activity, as measured by a delay in tumor growth and increased tumor regression using any of a variety of standard measures that have been described as useful with these models. An example of a protocol which can be utilized is provided below.

Efficacy study. Female athymic mice (CD-1 nu/nu, 8-12 weeks old) are obtained from Charles River Breeding Laboratories (Wilmington, Mass.) and are housed in a barrier. When mice are 7 to 8 week old, each mouse was inoculated with $1\times10^7$ Karpas cells (or another CD30 positive cell line adapted to growth in vivo) in 0.2 ml of medium in the right flank subcutaneously. The treatments are started when the tumor size reaches approximately 200 mm$^3$. Sheddase compound is dosed orally, subcutaneously or with mini-osmotic pumps implanted subcutaneously to give a blood concentration between 100 nM and 2 µM total concentration at trough and anti-CD30 antibody administered at doses of 0.1 to 1 mg/kg by intraperitoneal (IP) injection. Tumor sizes are measured twice weekly in two dimensions using a caliper, and the volume is presented in mm$^3$ using the formula: $V=0.5a\times b^2$, where a and b are the long and short diameters of the tumor, respectively. Tumor growth delay is measured as time (days) for the treated group to reach an arbitrary tumor size of 500-1000 mm3. Responses are designated as complete remissions (CR) when tumor volume decreases in size to the point of being undetectable (<3 mm×3 mm) and as partial remissions (PR) when tumor volume decreases to <50% of its starting volume.

Example C

In Human Clinical Studies

The clinical relevance of concomitantly treating a patient, carrying a CD30 bearing tumor, with a compound such as those described in this application with an anti-CD30 directed therapy (either antibody alone, an antibody fragment, or an antibody or fragment coupled to a cell toxic agent), could be examined clinically. Dosing of subjects with such tumors can be by oral route, by subcutaneous or intravenous injection of compound. Concomitantly treating with an anti-CD30 directed therapy should demonstrate additive, superadditive or synergistic activity, as measured using any of a variety of standard measures that have been described and accepted in standard clinical practice (e.g., RECIST criteria).

Each reference, including all patent, patent applications, and publications, cited in the present application is incorporated herein by reference in its entirety.

What is claimed is:

1. A method of treating a disease characterized by expression of CD30 or CD30 shedding selected from lymphoma, T-cell leukemia, and adult T-cell leukemia (ATL) in a human patient, comprising administering to said human patient:
   i) an antibody or antibody-conjugate which binds CD30; and
   ii) methyl (6S,7S)-7-[(hydroxyamino)carbonyl]-6-[(4-phenylpiperazin-1-yl)carbonyl]-5-azaspiro[2.5]octane-5-carboxylate, or a pharmaceutically acceptable salt thereof;

wherein the amount of said methyl (6S,7S)-7-[(hydroxyamino)carbonyl]-6-[(4-phenylpiperazin-1-yl)carbonyl]-5-azaspiro[2,5]octane-5-carboxylate, or said pharmaceutically acceptable salt thereof, and said antibody or antibody-conjugate together provide a therapeutically effective amount.

2. The method of claim 1 wherein said lymphoma is Hodgkin's disease (HD), Burkitt's lymphoma, anaplastic large-cell lymphoma (ALCL), cutaneous T-cell lymphoma, nodular small cleaved-cell lymphoma, lymphocytic lymphoma, peripheral T-cell lymphomas, Lennert's lymphoma, immunoblastic lymphoma, or entroblastic/centrocytic follicular lymphoma.

3. The method of claim 1 wherein said disease is T cell leukemia or adult T-cell leukemia (ATL).

4. The method of claim 1 wherein an antibody which binds CD30 is administered.

5. The method of claim 4 wherein said antibody is a monoclonal antibody.

6. The method of claim 4 wherein said antibody is a human, humanized, or chimeric antibody.

7. The method of claim 1 wherein an antibody-conjugate which binds CD30 is administered.

8. The method of claim 7 wherein said antibody-conjugate is an anti-CD30 antibody conjugated with a cytotoxin or radiotoxin.

9. The method of claim 8 wherein said antibody-conjugate is a monoclonal anti-CD30 antibody conjugated with a cytotoxin or radiotoxin.

10. The method of claim 9 wherein said antibody-conjugate is a human, humanized, or chimeric anti-CD30 antibody conjugated with a cytotoxin or radiotoxin.

11. The method of claim 1 wherein said administering is carried out such that the physiological effects of both said methyl (6S,7S)-7-[(hydroxyamino)carbonyl]-6-[(4-phenylpiperazin-1-yl)carbonyl]-5-azaspiro[2.5]octane-5-carboxylate, or said pharmaceutically acceptable salt thereof, and said antibody or antibody conjugate overlap in said patient.

12. The method of claim 1, wherein said disease is lymphoma.

UNITED STATES PATENT AND TRADEMARK OFFICE
CERTIFICATE OF CORRECTION

| | | |
|---|---|---|
| PATENT NO. | : 7,910,108 B2 | Page 1 of 1 |
| APPLICATION NO. | : 11/757600 | |
| DATED | : March 22, 2011 | |
| INVENTOR(S) | : Steven M. Friedman et al. | |

It is certified that error appears in the above-identified patent and that said Letters Patent is hereby corrected as shown below:

On the Title Page, Item (56) (Other Publications) delete "Inarimastat" and insert -- Marimastat --, therefor.

Col. 41, line 60 in Claim 1, delete "[2,5]" and insert -- [2.5] --, therefor.

Col. 42, line 2 in Claim 2, delete "entroblastic/centrocytic" and insert -- centroblastic/centrocytic --, therefor.

Col. 42, line 4 in Claim 3, delete "T cell" and insert -- T-cell --, therefor.

Signed and Sealed this
Twenty-eighth Day of June, 2011

David J. Kappos
*Director of the United States Patent and Trademark Office*

SEQUENCE LISTING

<160> NUMBER OF SEQ ID NOS: 12

<210> SEQ ID NO 1
<211> LENGTH: 348
<212> TYPE: PRT
<213> ORGANISM: Homo sapiens

<400> SEQUENCE: 1

Gly Ala Gly Gly Thr Gly Cys Ala Gly Thr Thr Gly Thr Gly Gly
1               5                   10                  15

Ala Gly Thr Cys Thr Gly Gly Gly Ala Gly Gly Cys Thr Thr
            20                  25                  30

Gly Gly Thr Cys Cys Ala Gly Cys Cys Thr Gly Gly Gly Gly Gly
            35                  40                  45

Thr Cys Cys Cys Thr Gly Ala Gly Ala Cys Thr Cys Cys Thr
    50                  55                  60

Gly Thr Gly Thr Ala Gly Cys Cys Thr Cys Thr Gly Gly Ala Thr Thr
65                  70                  75                  80

Cys Ala Cys Cys Thr Thr Thr Ala Gly Thr Ala Ala Cys Thr Cys Thr
                85                  90                  95

Thr Gly Gly Ala Thr Gly Ala Gly Cys Thr Gly Gly Gly Thr Cys Cys
            100                 105                 110

Gly Cys Cys Ala Gly Gly Cys Thr Cys Cys Ala Gly Gly Ala Ala
            115                 120                 125

Ala Gly Gly Gly Cys Thr Gly Gly Ala Gly Thr Gly Gly Gly Thr Gly
            130                 135                 140

Gly Cys Cys Ala Ala Cys Ala Thr Ala Ala Cys Gly Ala Ala Gly
145                 150                 155                 160

Ala Thr Gly Gly Ala Ala Gly Thr Gly Ala Gly Ala Ala Ala Thr Thr
                165                 170                 175

Cys Thr Ala Thr Gly Thr Gly Gly Ala Cys Thr Cys Thr Gly Thr Gly
            180                 185                 190

Ala Ala Gly Gly Gly Cys Cys Gly Ala Thr Thr Cys Ala Cys Cys Thr
            195                 200                 205

Thr Cys Thr Cys Cys Ala Gly Ala Gly Ala Cys Ala Ala Cys Gly Cys
    210                 215                 220

Cys Gly Ala Gly Ala Ala Cys Thr Cys Ala Cys Thr Gly Thr Ala Thr
225                 230                 235                 240

Cys Thr Gly Cys Ala Ala Ala Thr Gly Ala Ala Cys Ala Gly Cys Cys
                245                 250                 255

Thr Gly Ala Gly Ala Gly Cys Cys Gly Ala Gly Gly Ala Cys Ala Cys
            260                 265                 270

Gly Gly Cys Thr Gly Thr Gly Thr Ala Thr Thr Ala Cys Thr Gly Thr
            275                 280                 285

Gly Cys Gly Ala Gly Gly Thr Cys Ala Thr Thr Gly Gly Thr
            290                 295                 300

Ala Cys Thr Thr Cys Cys Ala Cys Thr Cys Thr Gly Gly Gly Gly
305                 310                 315                 320

Cys Cys Gly Thr Gly Gly Cys Ala Cys Cys Thr Gly Gly Thr Cys
                325                 330                 335

Ala Cys Thr Gly Thr Cys Thr Cys Cys Thr Cys Ala
            340                 345

<210> SEQ ID NO 2

<211> LENGTH: 116
<212> TYPE: PRT
<213> ORGANISM: Homo sapiens

<400> SEQUENCE: 2

```
Glu Val Gln Leu Val Glu Ser Gly Gly Gly Leu Val Gln Pro Gly Gly
  1               5                  10                  15

Ser Leu Arg Leu Ser Cys Val Ala Ser Gly Phe Thr Phe Ser Asn Ser
             20                  25                  30

Trp Met Ser Trp Val Arg Gln Ala Pro Gly Lys Gly Leu Glu Trp Val
         35                  40                  45

Ala Asn Ile Asn Glu Asp Gly Ser Glu Lys Phe Tyr Val Asp Ser Val
 50                  55                  60

Lys Gly Arg Phe Thr Phe Ser Arg Asp Asn Ala Glu Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Val His Trp Tyr Phe His Leu Trp Gly Arg Gly Thr Leu Val
            100                 105                 110

Thr Val Ser Ser
            115
```

<210> SEQ ID NO 3
<211> LENGTH: 324
<212> TYPE: PRT
<213> ORGANISM: Homo sapiens

<400> SEQUENCE: 3

```
Gly Ala Ala Ala Thr Gly Thr Gly Thr Gly Ala Cys Gly Cys
  1               5                  10                  15

Ala Gly Thr Cys Thr Cys Cys Ala Gly Gly Cys Ala Cys Cys Cys Thr
             20                  25                  30

Gly Thr Cys Thr Thr Thr Gly Thr Cys Thr Cys Cys Ala Gly Gly Gly
         35                  40                  45

Gly Ala Ala Ala Gly Ala Gly Cys Cys Ala Cys Cys Cys Thr Cys Thr
 50                  55                  60

Cys Cys Thr Gly Cys Ala Gly Gly Gly Cys Cys Ala Gly Thr Cys Ala
 65                  70                  75                  80

Gly Ala Gly Thr Gly Thr Thr Ala Gly Cys Ala Gly Cys Ala Gly Cys
             85                  90                  95

Thr Ala Cys Thr Thr Ala Gly Cys Cys Thr Gly Gly Thr Ala Cys Cys
            100                 105                 110

Ala Gly Cys Ala Gly Ala Ala Ala Cys Cys Thr Gly Gly Cys Cys Ala
            115                 120                 125

Gly Gly Cys Thr Cys Cys Cys Ala Gly Gly Cys Thr Cys Cys Thr Cys
        130                 135                 140

Ala Thr Cys Thr Ala Thr Gly Gly Thr Gly Cys Ala Thr Cys Cys Ala
145                 150                 155                 160

Gly Cys Ala Gly Gly Gly Cys Cys Ala Cys Thr Gly Gly Cys Ala Thr
            165                 170                 175

Cys Cys Cys Ala Gly Ala Cys Ala Gly Gly Thr Thr Cys Ala Gly Thr
            180                 185                 190

Gly Gly Cys Ala Gly Thr Gly Gly Gly Thr Cys Thr Gly Gly Gly Ala
            195                 200                 205

Cys Ala Gly Ala Cys Thr Thr Cys Ala Cys Thr Cys Thr Cys Ala Cys
        210                 215                 220
```

```
Cys Ala Thr Cys Ala Gly Cys Ala Gly Cys Cys Thr Gly Gly Ala Gly
225                 230                 235                 240

Cys Cys Thr Gly Ala Ala Gly Ala Thr Thr Thr Gly Cys Ala Gly
            245                 250                 255

Thr Gly Thr Ala Thr Thr Ala Cys Thr Gly Thr Cys Ala Gly Cys Ala
        260                 265                 270

Gly Thr Ala Thr Gly Gly Thr Ala Gly Cys Thr Cys Ala Cys Cys Gly
        275                 280                 285

Thr Gly Gly Ala Cys Gly Thr Thr Cys Gly Gly Cys Ala Ala Gly
        290                 295                 300

Gly Gly Ala Cys Cys Ala Ala Gly Gly Thr Gly Gly Ala Ala Ala Thr
305                 310                 315                 320

Cys Ala Ala Ala

<210> SEQ ID NO 4
<211> LENGTH: 108
<212> TYPE: PRT
<213> ORGANISM: Homo sapiens

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 5
<211> LENGTH: 348
<212> TYPE: PRT
<213> ORGANISM: Homo sapiens

<400> SEQUENCE: 5

Cys Ala Gly Gly Thr Gly Cys Ala Gly Cys Thr Ala Cys Ala Gly Cys
1               5                   10                  15

Ala Gly Thr Gly Gly Gly Gly Cys Gly Cys Ala Gly Gly Ala Cys Thr
            20                  25                  30

Gly Thr Thr Gly Ala Ala Gly Cys Cys Thr Cys Gly Gly Ala
        35                  40                  45

Ala Cys Cys Cys Thr Gly Thr Cys Cys Cys Thr Cys Ala Cys Cys Thr
    50                  55                  60

Gly Cys Gly Cys Thr Gly Thr Cys Thr Ala Thr Gly Gly Thr Gly Gly
65                  70                  75                  80

Gly Thr Cys Cys Thr Thr Cys Ala Gly Thr Gly Gly Thr Thr Ala Cys
                85                  90                  95

Thr Ala Cys Thr Gly Gly Ala Gly Cys Thr Gly Gly Ala Thr Cys Cys
            100                 105                 110

Gly Cys Cys Ala Gly Cys Cys Cys Cys Cys Ala Gly Gly Gly Ala Ala
        115                 120                 125
```

Gly Gly Gly Gly Cys Thr Gly Ala Gly Thr Gly Ala Thr
            130                 135                 140

Gly Gly Gly Gly Ala Ala Thr Cys Ala Thr Cys Ala Thr Ala
145                 150                 155                 160

Gly Thr Gly Gly Ala Ala Gly Cys Ala Cys Ala Ala Gly Thr Ala
            165                 170                 175

Cys Ala Cys Cys Cys Gly Thr Cys Cys Thr Cys Ala Ala Gly
            180                 185                 190

Ala Gly Cys Cys Gly Ala Gly Thr Cys Ala Cys Ala Thr Ala Thr
            195                 200                 205

Cys Ala Gly Thr Ala Gly Ala Cys Ala Cys Gly Thr Cys Cys Ala Ala
            210                 215                 220

Gly Cys Ala Cys Cys Ala Ala Thr Cys Thr Cys Cys Thr Gly
225                 230                 235                 240

Ala Ala Gly Cys Thr Gly Ala Gly Cys Thr Cys Thr Gly Thr Gly Ala
            245                 250                 255

Cys Cys Gly Cys Cys Gly Cys Gly Ala Cys Ala Cys Gly Gly Cys
            260                 265                 270

Thr Gly Thr Gly Thr Ala Thr Thr Ala Cys Thr Gly Thr Gly Cys Gly
            275                 280                 285

Ala Gly Ala Gly Ala Gly Ala Cys Thr Gly Thr Cys Thr Ala Cys Thr
290                 295                 300

Ala Cys Thr Thr Cys Gly Ala Thr Cys Thr Cys Thr Gly Gly Gly Gly
305                 310                 315                 320

Cys Cys Gly Thr Gly Gly Cys Ala Cys Cys Cys Thr Gly Gly Thr Cys
            325                 330                 335

Ala Cys Thr Gly Thr Cys Thr Cys Cys Thr Cys Ala
            340                 345

<210> SEQ ID NO 6
<211> LENGTH: 116
<212> TYPE: PRT
<213> ORGANISM: Homo sapiens

<400> SEQUENCE: 6

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Lys Tyr Thr Pro Ser Leu Lys
    50                  55                  60

Ser Arg Val Thr Ile Ser Val Asp Thr Ser Lys His Gln Phe Ser Leu
65                  70                  75                  80

Lys Leu Ser Ser Val Thr Ala Ala Asp Thr Ala Val Tyr Tyr Cys Ala
                85                  90                  95

Arg Glu Thr Val Tyr Tyr Phe Asp Leu Trp Gly Arg Gly Thr Leu Val
            100                 105                 110

Thr Val Ser Ser
        115

<210> SEQ ID NO 7
<211> LENGTH: 321
<212> TYPE: PRT
<213> ORGANISM: Homo sapiens

<400> SEQUENCE: 7

Gly Ala Ala Ala Thr Gly Thr Gly Thr Gly Ala Cys Ala Cys
1               5                   10                  15

Ala Gly Thr Cys Thr Cys Cys Ala Gly Cys Ala Cys Cys Thr
            20                  25                  30

Gly Thr Cys Thr Thr Gly Thr Cys Cys Ala Gly Gly Gly
        35                  40                  45

Gly Ala Ala Ala Gly Ala Gly Cys Cys Ala Cys Cys Thr Cys Thr
50                  55                      60

Cys Cys Thr Gly Cys Ala Gly Gly Cys Cys Ala Gly Thr Cys Ala
65                  70                  75                  80

Gly Ala Gly Thr Gly Thr Ala Ala Gly Cys Ala Gly Cys Ala Ala Cys
                85                  90                  95

Thr Thr Ala Gly Cys Cys Thr Gly Gly Thr Ala Cys Ala Ala Cys
                100                 105                 110

Ala Gly Ala Ala Ala Cys Cys Thr Gly Gly Cys Cys Ala Gly Gly Cys
            115                 120                 125

Thr Cys Cys Cys Ala Gly Gly Cys Thr Cys Cys Thr Cys Ala Thr Cys
130                 135                 140

Thr Ala Thr Gly Ala Thr Gly Cys Ala Thr Cys Cys Ala Ala Cys Ala
145                 150                 155                 160

Gly Gly Gly Cys Cys Ala Cys Thr Gly Gly Cys Ala Thr Cys Cys Cys
                165                 170                 175

Ala Gly Cys Cys Ala Gly Gly Cys Thr Cys Ala Gly Thr Gly Gly Cys
                180                 185                 190

Ala Gly Thr Gly Gly Gly Thr Cys Thr Gly Gly Gly Ala Cys Ala Gly
                195                 200                 205

Ala Cys Thr Thr Cys Ala Cys Thr Cys Thr Cys Ala Cys Cys Ala Thr
                210                 215                 220

Cys Ala Gly Cys Ala Gly Cys Cys Thr Ala Gly Ala Gly Cys Cys Thr
225                 230                 235                 240

Gly Ala Ala Gly Ala Thr Thr Thr Thr Gly Cys Ala Gly Thr Thr Thr
                245                 250                 255

Ala Thr Thr Ala Cys Thr Gly Thr Cys Ala Ala Cys Ala Gly Cys Gly
                260                 265                 270

Thr Ala Gly Cys Ala Ala Cys Thr Gly Gly Cys Cys Gly Thr Gly Gly
            275                 280                 285

Ala Cys Gly Thr Thr Cys Gly Gly Cys Cys Ala Ala Gly Gly Gly Ala
            290                 295                 300

Cys Cys Ala Ala Gly Gly Thr Gly Gly Ala Ala Ala Thr Cys Ala Ala
305                 310                 315                 320

Ala

<210> SEQ ID NO 8
<211> LENGTH: 107
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile

```
                35                  40                  45
Tyr Asp Ala Ser Asn Arg Ala Thr Gly Ile Pro Ala Arg Leu Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
            100                 105

<210> SEQ ID NO 9
<211> LENGTH: 336
<212> TYPE: PRT
<213> ORGANISM: Homo sapiens

<400> SEQUENCE: 9

Cys Ala Gly Gly Thr Gly Cys Ala Gly Cys Thr Ala Cys Ala Gly Cys
 1               5                  10                  15

Ala Gly Thr Gly Gly Gly Gly Cys Gly Cys Ala Gly Gly Ala Cys Thr
                20                  25                  30

Gly Thr Thr Gly Ala Ala Gly Cys Cys Thr Thr Cys Gly Gly Ala Gly
            35                  40                  45

Ala Cys Cys Cys Thr Gly Thr Cys Cys Cys Thr Cys Ala Cys Cys Thr
 50                  55                  60

Gly Cys Gly Cys Thr Gly Thr Cys Thr Ala Thr Gly Gly Thr Gly Gly
65                  70                  75                  80

Gly Thr Cys Cys Thr Thr Cys Ala Gly Thr Gly Cys Thr Thr Ala Cys
                85                  90                  95

Thr Ala Cys Thr Gly Gly Ala Gly Cys Thr Gly Gly Ala Thr Cys Cys
            100                 105                 110

Gly Cys Cys Ala Gly Cys Cys Cys Cys Ala Gly Gly Gly Ala Ala Gly
            115                 120                 125

Gly Gly Gly Gly Cys Thr Gly Gly Ala Gly Thr Gly Gly Ala Thr Thr
130                 135                 140

Gly Gly Gly Gly Ala Cys Ala Thr Cys Ala Ala Thr Cys Ala Thr Gly
145                 150                 155                 160

Gly Thr Gly Gly Ala Gly Gly Cys Ala Cys Cys Ala Ala Cys Thr Ala
                165                 170                 175

Cys Ala Ala Cys Cys Cys Gly Thr Cys Cys Cys Thr Cys Ala Ala Gly
                180                 185                 190

Ala Gly Thr Cys Gly Ala Gly Thr Cys Ala Cys Cys Ala Thr Ala Thr
                195                 200                 205

Cys Ala Gly Thr Ala Gly Ala Cys Ala Cys Gly Thr Cys Cys Ala Ala
            210                 215                 220

Gly Ala Ala Cys Cys Ala Gly Thr Thr Cys Thr Cys Cys Cys Thr Gly
225                 230                 235                 240

Ala Ala Gly Cys Thr Gly Ala Ala Cys Thr Cys Thr Gly Thr Ala Ala
                245                 250                 255

Cys Cys Gly Cys Cys Gly Cys Gly Gly Ala Cys Ala Cys Gly Gly Cys
            260                 265                 270

Thr Gly Thr Gly Thr Ala Thr Thr Ala Cys Thr Gly Thr Gly Cys Gly
            275                 280                 285

Ala Gly Cys Cys Thr Ala Ala Cys Thr Gly Cys Cys Thr Ala Cys Thr
            290                 295                 300

Gly Gly Gly Gly Cys Cys Ala Gly Gly Gly Ala Ala Gly Cys Cys Thr
```

```
                305                 310                 315                 320
Gly Gly Thr Cys Ala Cys Cys Gly Thr Cys Thr Cys Cys Thr Cys Ala
                    325                 330                 335

<210> SEQ ID NO 10
<211> LENGTH: 112
<212> TYPE: PRT
<213> ORGANISM: Homo sapiens

<400> SEQUENCE: 10

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Ala Tyr
                20                  25                  30

Tyr Trp Ser Trp Ile Arg Gln Pro Pro Gly Lys Gly Leu Glu Trp Ile
            35                  40                  45

Gly Asp Ile Asn His Gly Gly Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Ser Leu Thr Ala Tyr Trp Gly Gln Gly Ser Leu Val Thr Val Ser Ser
                100                 105                 110

<210> SEQ ID NO 11
<211> LENGTH: 321
<212> TYPE: PRT
<213> ORGANISM: Homo sapiens

<400> SEQUENCE: 11

Gly Ala Cys Ala Thr Cys Cys Ala Gly Ala Thr Gly Ala Cys Cys Cys
 1               5                  10                  15

Ala Gly Thr Cys Thr Cys Cys Ala Ala Cys Cys Thr Cys Cys Cys Thr
                20                  25                  30

Gly Thr Cys Thr Gly Cys Ala Thr Cys Thr Gly Thr Ala Gly Gly Ala
            35                  40                  45

Gly Ala Cys Ala Gly Ala Gly Thr Cys Ala Cys Cys Ala Thr Cys Ala
    50                  55                  60

Cys Thr Thr Gly Thr Cys Gly Gly Gly Cys Gly Ala Gly Thr Cys Ala
65                  70                  75                  80

Gly Gly Gly Thr Ala Thr Thr Ala Gly Cys Ala Gly Cys Thr Gly Gly
                85                  90                  95

Thr Thr Ala Ala Cys Cys Thr Gly Gly Thr Ala Thr Cys Ala Gly Cys
                100                 105                 110

Ala Gly Ala Ala Ala Cys Cys Ala Gly Ala Gly Ala Ala Ala Gly Cys
            115                 120                 125

Cys Cys Cys Thr Ala Ala Gly Thr Cys Cys Cys Thr Gly Ala Thr Cys
    130                 135                 140

Thr Ala Thr Gly Cys Thr Gly Cys Ala Thr Cys Cys Ala Gly Thr Thr
145                 150                 155                 160

Thr Gly Cys Ala Ala Ala Gly Thr Gly Gly Gly Gly Thr Cys Cys Cys
                165                 170                 175

Ala Thr Cys Ala Ala Gly Gly Thr Thr Cys Ala Gly Cys Gly Gly Cys
                180                 185                 190

Ala Gly Thr Gly Gly Ala Thr Cys Thr Gly Gly Gly Ala Cys Ala Gly
            195                 200                 205
```

```
Ala Thr Thr Thr Cys Ala Cys Thr Cys Thr Cys Ala Cys Cys Ala Thr
        210                 215                 220

Cys Ala Gly Cys Ala Gly Cys Cys Thr Gly Cys Ala Gly Cys Cys Thr
225                 230                 235                 240

Gly Ala Ala Gly Ala Thr Thr Thr Thr Gly Cys Ala Ala Cys Thr Thr
                245                 250                 255

Ala Thr Thr Ala Cys Thr Gly Cys Cys Ala Ala Cys Ala Gly Thr Ala
            260                 265                 270

Thr Gly Ala Thr Ala Gly Thr Thr Ala Cys Cys Cys Thr Ala Thr Cys
        275                 280                 285

Ala Cys Cys Thr Thr Cys Gly Gly Cys Cys Ala Ala Gly Gly Gly Ala
        290                 295                 300

Cys Ala Cys Gly Ala Cys Thr Gly Gly Ala Gly Ala Thr Thr Ala Ala
305                 310                 315                 320

Ala

<210> SEQ ID NO 12
<211> LENGTH: 112
<212> TYPE: PRT
<213> ORGANISM: Homo sapiens

<400> SEQUENCE: 12

Asp Ile Gln Met Thr Gln Ser Pro Ala Thr Ile Glu Asn Thr Ser Leu
1               5                   10                  15

Ser Ala Ser Val Gly Asp Arg Val Thr Ile Thr Cys Arg Ala Ser Gln
            20                  25                  30

Gly Ile Ser Ser Trp Leu Thr Trp Tyr Gln Gln Lys Pro Glu Lys Ala
        35                  40                  45

Pro Lys Ser Leu Ile Tyr Ala Ala Ser Ser Leu Gln Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Tyr
                85                  90                  95

Asp Ser Tyr Pro Ile Thr Phe Gly Gln Gly Thr Arg Leu Glu Ile Lys
            100                 105                 110
```